(12) United States Patent
Thaxton et al.

(10) Patent No.: US 10,568,898 B2
(45) Date of Patent: Feb. 25, 2020

(54) LIPOPHILIC NANOPARTICLES FOR DRUG DELIVERY

(71) Applicant: Northwestern University, Evanston, IL (US)

(72) Inventors: C. Shad Thaxton, Chicago, IL (US); Leo I. Gordon, Winnetka, IL (US); Raja Kannan Mutharasan, Chicago, IL (US); Casey N. Grun, Tigard, OR (US); Linda Foit, Chicago, IL (US)

(73) Assignee: Northwestern University, Evanston, IL (US)

( * ) Notice: Subject to any disclaimer, the term of this patent is extended or adjusted under 35 U.S.C. 154(b) by 46 days.

(21) Appl. No.: 14/911,957

(22) PCT Filed: Aug. 13, 2014

(86) PCT No.: PCT/US2014/050963
§ 371 (c)(1),
(2) Date: Feb. 12, 2016

(87) PCT Pub. No.: WO2015/023797
PCT Pub. Date: Feb. 19, 2015

(65) Prior Publication Data
US 2016/0193361 A1    Jul. 7, 2016

Related U.S. Application Data

(60) Provisional application No. 61/865,551, filed on Aug. 13, 2013.

(51) Int. Cl.
*A61K 47/54* (2017.01)
*A61K 31/704* (2006.01)
*A61K 31/475* (2006.01)

(52) U.S. Cl.
CPC .......... *A61K 31/704* (2013.01); *A61K 31/475* (2013.01)

(58) Field of Classification Search
None
See application file for complete search history.

(56) References Cited

U.S. PATENT DOCUMENTS

| 5,264,618 A * | 11/1993 | Felgner ............... A61K 9/0014 |
| | | 530/323 |
| 5,472,881 A | 12/1995 | Beebe et al. |
| 5,814,666 A | 9/1998 | Green et al. |
| 6,361,944 B1 | 3/2002 | Mirkin et al. |
| 6,506,564 B1 | 1/2003 | Mirkin et al. |
| 7,129,222 B2 | 10/2006 | van Nest et al. |
| 7,563,618 B2 | 7/2009 | Gryaznov et al. |
| 7,615,539 B2 | 11/2009 | Uhlmann et al. |
| 8,008,267 B2 | 8/2011 | Kandimalla et al. |
| 8,124,590 B2 | 2/2012 | van Nest et al. |
| 8,323,686 B2 | 12/2012 | Mirkin et al. |
| 8,586,555 B2 | 11/2013 | Fearon et al. |
| 9,216,155 B2 | 12/2015 | Thaxton et al. |
| 9,532,948 B2 | 1/2017 | Mirkin et al. |
| 9,868,955 B2 | 1/2018 | Guiducci et al. |
| 9,999,673 B2 | 6/2018 | Rajeev et al. |
| 10,029,016 B2 | 7/2018 | Irvine et al. |
| 2002/0172711 A1 | 11/2002 | Martin et al. |
| 2003/0147966 A1 | 8/2003 | Franzen et al. |
| 2003/0170162 A1 | 9/2003 | Nayfeh et al. |
| 2004/0038891 A1 | 2/2004 | Bisgaier et al. |
| 2004/0053384 A1 | 3/2004 | Sligar et al. |
| 2004/0170560 A1 * | 9/2004 | Fossheim ............... A61K 9/127 |
| | | 424/1.29 |
| 2005/0090671 A1 | 4/2005 | Chang et al. |
| 2006/0083781 A1 | 4/2006 | Shastri et al. |
| 2006/0292174 A1 | 12/2006 | De Los Rios et al. |
| 2007/0218501 A1 | 9/2007 | Fogelman et al. |
| 2007/0243136 A1 | 10/2007 | Fisher et al. |
| 2007/0298257 A1 | 12/2007 | Ludwig et al. |
| 2008/0181928 A1 | 7/2008 | Hakimi-Mehr et al. |
| 2008/0194463 A1 | 8/2008 | Weller et al. |
| 2008/0274454 A1 | 11/2008 | Mirkin et al. |
| 2008/0306016 A1 | 12/2008 | Mirkin et al. |
| 2008/0311182 A1 | 12/2008 | Ferrari et al. |
| 2009/0209629 A1 | 8/2009 | Mirkin et al. |
| 2009/0317802 A1 | 12/2009 | Bhatia et al. |
| 2009/0324706 A1 | 12/2009 | Mirkin et al. |
| 2010/0136682 A1 | 6/2010 | Mirkin et al. |
| 2010/0144848 A1 | 6/2010 | Vogel et al. |
| 2010/0166842 A1 | 7/2010 | Lu et al. |

(Continued)

FOREIGN PATENT DOCUMENTS

CN    102036652 A    4/2011
CN    102165061 A    8/2011

(Continued)

OTHER PUBLICATIONS

International Search Report and Written Opinion for International Application No. PCT/US2009/002540 dated Jul. 22, 2010.
International Preliminary Report on Patentability for International Application No. PCT/US2009/002540 dated Nov. 4, 2010.
International Search Report and Written Opinion for International Application No. PCT/US2011/021753 dated Oct. 7, 2011.
International Preliminary Report on Patentability for International Application No. PCT/US2011/021753 dated Aug. 2, 2012.
International Search Report and Written Opinion for International Application No. PCT/US2013/027431 dated Jun. 13, 2013.
International Preliminary Report on Patentability for International Application No. PCT/US2013/027431 dated Sep. 4, 2014.

(Continued)

*Primary Examiner* — Jessica Worsham
(74) *Attorney, Agent, or Firm* — Wolf, Greenfield & Sacks, P.C.

(57) ABSTRACT

Nanostructures having a core, a lipid layer and a lipoprotein which are useful for delivering therapeutic agents are provided herein. Methods of treating disease using the nanostructures are also provided, including methods of treating cancer, infectious disease, vascular disease etc.

19 Claims, 26 Drawing Sheets

(56) References Cited

U.S. PATENT DOCUMENTS

| | | | |
|---|---|---|---|
| 2010/0184844 A1 | 7/2010 | Mirkin et al. | |
| 2010/0233141 A1 | 9/2010 | Polach et al. | |
| 2010/0233270 A1 | 9/2010 | Mirkin et al. | |
| 2011/0052680 A1 | 3/2011 | Hendrickson | |
| 2011/0111974 A1 | 5/2011 | Mirkin et al. | |
| 2012/0244230 A1 | 9/2012 | Mirkin et al. | |
| 2013/0034599 A1* | 2/2013 | Thaxton | A61K 9/127 424/450 |
| 2013/0089614 A1 | 4/2013 | Zhang et al. | |
| 2013/0101512 A1 | 4/2013 | Mirkin et al. | |
| 2013/0123333 A1 | 5/2013 | Mirkin et al. | |
| 2013/0195759 A1 | 8/2013 | Mirkin et al. | |
| 2013/0252852 A1 | 9/2013 | Pfeiffer et al. | |
| 2014/0005258 A1 | 1/2014 | Mirkin et al. | |
| 2014/0065425 A1 | 3/2014 | Bogdanov | |
| 2014/0294927 A1 | 10/2014 | Thaxton et al. | |
| 2015/0064255 A1 | 3/2015 | Thaxton et al. | |
| 2015/0086985 A1 | 3/2015 | Giljohann et al. | |
| 2016/0274134 A1 | 9/2016 | Mutharasan et al. | |
| 2016/0310425 A1 | 10/2016 | Mirkin et al. | |
| 2016/0348114 A1 | 12/2016 | Kleuss et al. | |

FOREIGN PATENT DOCUMENTS

| | | |
|---|---|---|
| JP | 2011-507807 | 3/2011 |
| JP | 2011-518826 A | 6/2011 |
| KR | 2011/0039798 A | 4/2011 |
| WO | WO 92/21330 | 12/1992 |
| WO | WO 2003/008539 A2 | 1/2003 |
| WO | WO 2005/063201 A2 | 7/2005 |
| WO | WO 2005/063288 A1 | 7/2005 |
| WO | WO 2006/110350 A2 | 10/2006 |
| WO | WO 2006/110350 A3 | 10/2006 |
| WO | WO 2006/128121 A2 | 11/2006 |
| WO | WO 2006/138145 A1 | 12/2006 |
| WO | WO 2007/008463 A2 | 1/2007 |
| WO | WO 2007/044851 A2 | 4/2007 |
| WO | WO 2007/089607 A2 | 8/2007 |
| WO | WO 2007/106683 A2 | 9/2007 |
| WO | WO 2008/127789 A2 | 10/2008 |
| WO | WO 2009/051451 A2 | 4/2009 |
| WO | WO 2009/061515 A1 | 5/2009 |
| WO | WO 2009/073984 A1 | 6/2009 |
| WO | WO 2009/120887 A2 | 10/2009 |
| WO | WO 2009/131704 A1 | 10/2009 |
| WO | WO 2009/131704 A2 | 10/2009 |
| WO | WO 2010/091293 A1 | 8/2010 |
| WO | WO 2010/105209 A1 | 9/2010 |
| WO | WO 2010/120420 A1 | 10/2010 |
| WO | WO 2010/148249 A1 | 12/2010 |
| WO | WO 2011/017456 A2 | 2/2011 |
| WO | WO 2011/017690 A2 | 2/2011 |
| WO | WO 2011/053940 A2 | 5/2011 |
| WO | WO 2011/072133 A1 | 6/2011 |
| WO | WO 2011/079290 A1 | 6/2011 |
| WO | WO 2011/091065 A2 | 7/2011 |
| WO | WO 2011/113054 A2 | 9/2011 |
| WO | 2012/006634 A2 | 1/2012 |
| WO | WO 2012/084991 A1 | 6/2012 |
| WO | WO 2013/036974 A1 | 3/2013 |
| WO | WO 2013/126776 A1 | 8/2013 |
| WO | WO 2013/151771 A1 | 10/2013 |
| WO | WO 2014/025795 A1 | 2/2014 |
| WO | WO 2014/175836 A1 | 10/2014 |
| WO | WO 2015/013673 A1 | 1/2015 |
| WO | WO 2015/013675 A1 | 1/2015 |
| WO | WO 2015/023797 A1 | 2/2015 |
| WO | WO 2015/153975 A1 | 10/2015 |
| WO | WO 2015/187966 A1 | 12/2015 |
| WO | WO 2016/004168 A1 | 1/2016 |
| WO | WO 2016/057549 A1 | 4/2016 |
| WO | WO 2016/115320 A1 | 7/2016 |
| WO | WO 2017/035278 A1 | 3/2017 |

OTHER PUBLICATIONS

International Search Report and Written Opinion for International Application No. PCT/US2014/050963 dated Dec. 3, 2014.

International Preliminary Report on Patentability for International Application No. PCT/US2014/050963 dated Feb. 25, 2016.

International Search Report and Written Opinion for International Application No. PCT/US2015/062431 dated Feb. 25, 2016.

Acton et al., Identification of scavenger receptor SR-BI as a high density lipoprotein receptor. Science. Jan. 26, 1996;271(5248):518-20.

Akhter et al., Gold nanoparticles in theranostic oncology: current state-of-the-art. Expert Opin Drug Deliv. Oct. 2012;9(10):1225-43. Epub Aug. 16, 2012.

Bae et al., Targeted drug delivery to tumors: myths, reality and possibility. J Control Release. Aug. 10, 2011;153(3):198-205. doi: 10.1016/j.jconrel.2011.06.001. Epub Jun. 6, 2011.

Banchelli, M. et al., "Phospholipid Membranes Decorated by Cholesterol-Based Oligonucleotides as Soft Hybrid Nanostructures," J. Phys. Chem., 2008, 112 (35), 10942-10952.

Barth et al., Scavenger receptor class B is required for hepatitis C virus uptake and cross-presentation by human dendritic cells. J Virol. Apr. 2008;82(7):3466-79. Epub Jan. 23, 2008.

Bhattarai et al., "Enhanced Gene and siRNA Delivery by Polycation-Modified Mesoporous Silica Nanoparticles Loaded with Chloroquine," Pharm. Res., 2010, 27, 2556-2568.

Chen et al., Kinetics and thermodynamics of DNA hybridization on gold nanoparticles. Nucleic Acids Res. Jun. 2009;37(11):3756-65. doi: 10.1093/nar/gkp230. Epub Apr. 20, 2009.

Cheng et al., Interdigitated phospholipid/alkanethiol bilayers assembled on APTMS-supported gold colloid electrodes. Electroanalysis. 2004;16(1-2):127-31. doi:10.1002/elan.200302929.

Cho et al., Therapeutic nanoparticles for drug delivery in cancer. Clin Cancer Res. Mar. 1, 2008;14(5):1310-6. doi: 10.1158/1078-0432.CCR-07-1441.

Chromy, B. et al., "Different Apolipoproteins Impact Nanolipoprotein Particle Formation," J. Am. Chem. Soc., 2007, 129 (46), 14348-14354.

Cormode, D.P. et al., "Nanocrystal Core High-Density Lipoproteins: A Multimodality Contrast Agent Platform," Nano Lett., 2008, 8 (11), 3715-3723.

Cutler et al., Polyvalent nucleic acid nanostructures. J Am Chem Soc. Jun. 22, 2011;133(24):9254-7. doi:10.1021/ja203375n. Epub Jun. 1, 2011.

Cutler et al., Polyvalent oligonucleotide iron oxide nanoparticle "click" conjugates. Nano Lett. Apr. 14, 2010;10(4):1477-80. doi:10.1021/nl100477m.

Daniel et al., Gold nanoparticles: assembly, supramolecular chemistry, quantum-size-related properties, and applications toward biology, catalysis, and nanotechnology. Chem Rev. Jan. 2004;104(1):293-346.

Dessi et al., Role of cholesterol synthesis and esterification in the growth of CEM and MOLT4 lymphoblastic cells. Biochem J. Feb. 1, 1997;321 ( Pt 3):603-8.

Dhar et al., Polyvalent oligonucleotide gold nanoparticle conjugates as delivery vehicles for platinum (IV) warheads. J Am Chem Soc. Oct. 21, 2009;131(41):14652-3. doi: 10.1021/ja907182.

Elbakry, A. et al., Layer-by-Layer Assembled Gold Nanoparticles for siRNA Delivery, Nano Lett., 2009, 9 (5), 2059-2064.

Fan, Arrays, H. et al., Self-Assembly of Ordered, Robust, Three-Dimensional Gold Nanocrystal/Silica Science, 2004, 403, 567-571.

Ferrari, Cancer nanotechnology: opportunities and challenges. Nature Reviews Cancer. 2005;5: 161-71.

Frias, J. C. et al., " Recombinant HDL-Like Nanoparticles: A Specific Contrast Agent for MRI of Atherosclerotic Plaques," J. Am. Chem. Soc., 2004, 126 (50), 16316-16317.

Frias, J. C. et al., "Properties of a Versatile Nanoparticle Platform Contrast Agent to Image and Characterize Atherosclerotic Plaques by Magnetic Resonance Imaging," Nano Lett., 2006, 6 (10), 2220-2224.

Giljohann et al., Gene regulation with polyvalent siRNA-nanoparticle conjugates. J Am Chem Soc. Feb. 18, 2009;131(6):2072-3.

(56) References Cited

OTHER PUBLICATIONS

Giljohann et al., Gold nanoparticles for biology and medicine. Angew Chem Int Ed Engl. Apr. 26, 2010;49(19):3280-94. doi: 10.1002/anie.200904359.
Giljohann et al., Oligonucleotide loading determines cellular uptake of DNA-modified gold nanoparticles. Nano Lett. Dec. 2007;7(12):3818-21. Epub Nov. 13, 2007.
Godard, G. et al., "Antisense Effects of Cholesterol-Oligodeoxynucleotide Conjugates Associated with Poly(alkylcyanoacrylate) Nanoparticles," Eur. J. Biochem., 1995, 232 (2), 404-410.
Goncalves et al., Uptake of high density lipoprotein (HDL) cholesteryl esters by human acute leukemia cells. Leuk Res. Aug. 2005;29(8):955-9. Epub Feb. 24, 2005.
Graziani et al., Uptake of a cholesterol-rich emulsion by breast cancer. Gynecol Oncol. Jun. 2002;85(3):493-7.
Grijalvo et al., Oligonucleotide delivery: a patent review (2010-2013). Expert Opin Ther Pat. Jul. 2014;24(7):801-19. doi:10.1517/13543776.2014.915944. Epub May 5, 2014.
Han et al., Drug and gene delivery using gold nanoparticles. NanoBiotechnology. Mar. 2007;3(1):40-5.
He et al., Phospholipid-stabilized Au-nanoparticles. Biomacromolecules. May-Jun. 2005;6(3):1224-5.
Hurst, S. et al., Maximizing DNA Loading on a Range of Gold Nanoparticle Sizes, Anal. Chem., 2006, 78 (24), 8313-8318.
Ji et al., Scavenger receptor BI promotes high density lipoprotein-mediated cellular cholesterol efflux. J Biol Chem. Aug. 22, 1997;272(34):20982-5.
Jones, Simultaneous labeling of lipoprotein intracellular trafficking in pigeon monocyte-derived macrophages. Am J Pathol. Mar. 1997;150(3):1113-24.
Katzman et al., Cholesterol-dependent infection of Burkitt's lymphoma cell lines by Epstein-Barr virus. J Gen Virol. Nov. 2003;84(Pt 11):2987-92.
Kim, S. et al., Systemic and Specific Delivery of Small Interfering RNAs to the Liver Mediated by Apolipoprotein A-I, Mol. Ther., 2007, 15 (6), 1145-1152.
Leander, D., "Mixed-Monolayer Gold Nanoparticles for Cancer Therapeutics," Nanoscape, 2010, 7 (1), 11-14.
Lee et al., All-in-one target-cell-specific magnetic nanoparticles for simultaneous molecular imaging and siRNA delivery. Angew Chem Int Ed Engl. 2009;48(23):4174-9. doi:10.1002/anie.200805998.
Leon et al., Alterations in cholesterol regulation contribute to the production of intratumoral androgens during progression to castration-resistant prostate cancer in a mouse xenograft model. Prostate. Mar. 1, 2010;70(4):390-400. doi: 10.1002/pros.21072.
Liu, J. et al., "Silica Nanoparticle Supported Lipid Bilayers for Gene Delivery," Chem. Commun., 2009, 5100-5102.
Luthi et al., Nanotechnology for synthetic high-density lipoproteins. Trens Mol Med. Dec. 2010;16(12):553-60. doi: 10.1016/j.molmed.2010.10.006. Epub Nov. 17, 2010.
Luthi et al., Tailoring of biomimetic high-density lipoprotein nanostructures changes cholesterol binding and efflux. ACS Nano. Jan. 24, 2012;6(1):276-85. doi: 10.1021/nn2035457. Epub Dec. 1, 2011.
Lytton-Jean et al., A thermodynamic investigation into the binding properties of DNA functionalized gold nanoparticle probes and molecular fluorophore probes. J Am Chem Soc. Sep. 21, 2005;127(37):12754-5.
Major, M. et al., "Characterisation and Phase Behaviour of Phospholipid Bilayers Adsorbed on Spherical Polysaccharidic Nanoparticles," Biochimica et Biophysica Acta, 1997, 1327, 32-40.
Massich et al., Regulating immune response using polyvalent nucleic acid-gold nanoparticle conjugates. Mol Pharm. Nov.-Dec. 2009;6(6):1934-40.
Matsunaga, T. et al., "Biomagnetic Nanoparticle Formation and Application," Supramolecular Science, 1998, 5 (3-4), 391-394.
McMahon et al., Biomimetic high density lipoprotein nanoparticles for nucleic acid delivery. Nano Lett. Mar. 9, 2011;11(3):1208-14. doi: 10.1021/nl1041947. Epub Feb. 14, 2011.
Mirza et al., Preparation and characterization of doxorubicin functionalized gold nanoparticles. Eur J Med Chem. May 2011;46(5):1857-60. doi: 10.1016/j.ejmech.2011.02.048. Epub Feb. 24, 2011.
Mulas et al., Cholesterol esters as growth regulators of lymphocytic leukaemia cells. Cell Prolif. Aug. 2011;44(4):360-71. doi: 10.1111/j.1365-2184.2011.00758.x. Epub Jun. 6, 2011.
Niemeyer, C. et al., "Bifunctional DNA-Gold Nanoparticle Conjugates as Building Blocks for the Self-Assembly of Cross-Linked Particle Layers," Biochemical and Biophysical Research Communications, 2003, 311 (4), 995-999.
Nikolov et al., Bias-dependent admittance in hybrid bilayer membranes. Langmuir. Aug. 15, 2006;22(17):7156-8.
Patel et al., Peptide antisense nanoparticles. Proc Natl Acad Sci U S A. Nov. 11, 2008;105(45):17222-6. doi:10.1073/pnas.0801609105.
Patil et al., "Evidence for Novel Interdigitated Bilayer Formation of Fatty Acids During Three-Dimensional Self-Assembly on Silver Colloidal Particles," J. Am. Chem. Soc., 1997, 119 (39), 9281-9282.
Paul, New Way to Kill Lymphoma without Chemotherapy uses Golden Nanoparticles. Feinberg School of Medicine: Northwestern University. Jan. 22. 2013. 4 pages. ww.feinberg.northwestern.edu/news/2013/01/lymphoma_nanoparticales.html.
Rader et al., The role of reverse cholesterol transport in animals and humans and relationship toatherosclerosis. J Lipid Res. Apr. 2009;50 Suppl:S189-94. Epub Dec. 8, 2008.
Rana et al., Monolayer coated gold nanoparticles for delivery applications. Adv Drug Deliv Rev. Feb. 2012;64(2):200-16. doi: 10.1016/j.addr.2011.08.006. Epub Sep. 6, 2011.
Rosi et al., Oligonucleotide-modified gold nanoparticles for intracellular gene regulation. Science. May 19, 2006;312(5776):1027-30.
Rothblat et al., Cell cholesterol efflux: integration of old and new observations provides new insights. J Lipid Res. May 1999;40(5):781-96.
Seferos et al., Polyvalent DNA nanoparticle conjugates stabilize nucleic acids. Nano Lett. Jan. 2009;9(1):308-11.
Shahzad et al., Targeted delivery of small interfering RNA using reconstituted high-density lipoprotein nanoparticles. Neoplasia. Apr. 2011;13(4):309-19.
Shin et al., pH-responsive high-density lipoprotein-like nanoparticles to release paclitaxel at acidic pH in cancer chemotherapy. Int J Nanomedicine. 2012;7:2805-16. doi: 10.2147/IJN.S29817. Epub Jun. 6, 2012.
Sigalov, A novel ligand-independent peptide inhibitor of TREM-1 suppresses tumor growth in human lung cancer xenografts and prolongs survival of mice with lipopolysaccharide-induced septic shock. Int Immunopharmacol. Jul. 2014;21(1):208-19. doi: 10.1016/j.intimp.2014.05.001. Epub May 14, 2014.
Sood, 'Good cholesterol' nanoparticles seek and destroy cancer cells. The University of Texas MD Anderson Cancer Center. 2011. Downloaded Apr. 4, 2011. http://healthorbit.ca/newsdetail.asp?opt=1&nltid=164032911.
Thaxton, C.S. et al., "Templated Spherical High Density Lipoprotein Nanoparticles," J. Am. Chem. Soc., 2009, 131 (4), 1384-1385.
Tiwari et al., Functionalized gold nanoparticles and their biomedical applications. Nanomaterials. 2011;1:31-63. doi: 10.3390/nano1010031.
Tripathy et al., High Density Lipoprotein Nanoparticles Deliver RNAi to Endothelial Cells to Inhibit Angiogenesis. Part Part Syst Charact. Nov. 1, 2014;31(11):1141-1150.
Wang et al., Doxorubicin-tethered responsive gold nanoparticles facilitate intracellular drug delivery for overcoming multidrug resistance in cancer cells. ACS Nano. May 24, 2011;5(5):3679-92. doi: 10.1021/nn200007z. Epub Apr. 12, 2011.
Wei et al., Polyvalent immunostimulatory nanoagents with self-assembled CpG oligonucleotide-conjugated gold nanoparticles. Angew Chem Int Ed Engl. Jan. 27, 2012;51(5):1202-6. doi:10.1002/anie.201105187. Epub Dec. 21, 2011.
Wolfrum et al., Mechanisms and optimization of in vivo delivery of lipophilic siRNAs. Nat Biotechnol. Oct. 2007;25(10):1149-57. Epub Sep. 16, 2007.
Yang et al., Biomimetic, synthetic HDL nanostructures for lymphoma. Proc Natl Acad Sci U S A. Feb. 12, 2013;110(7):2511-6. doi: 10.1073/pnas.1213657110. Epub Jan. 23, 2013.

(56) References Cited

OTHER PUBLICATIONS

Zhang et al., A general approach to DNA-programmable atom equivalents. Nat Mater. Aug. 2013;12(8):741-6. doi: 10.1038/nmat3647. Epub May 19, 2013.
Zhang et al., Nanopod formation through gold nanoparticle templated and catalyzed crosslinking of polymers bearing pendant propargyl ethers. J Am Chem Soc. Nov. 3, 2010;132(43):15151-3.
Zhang et al., Self-assembled monolayers of terminal alkynes on gold. J Am Chem Soc. Apr. 25, 2007;129(16):4876-7. Epub Mar. 31, 2007.
U.S. Appl. No. 14/907,430, filed Jan. 25, 2016, Radovic-Moreno et al.
U.S. Appl. No. 14/907,455, filed Jan. 25, 2016, Gryaznov et al.
U.S. Appl. No. 14/963,881, filed Dec. 9, 2015, Thaxton et al.
U.S. Appl. No. 15/073,941, filed Mar. 18, 2016, Mutharasan et al.
Boudreault et al., Nanoscale tools to selectively destroy cancer cells. Chem Commun. May 14, 2008;(18):2118-20. doi: 10.1039/b800528a. Epub Apr. 7, 2008.
Cho et al., Targeted delivery of siRNA-generating DNA nanocassettes using multifunctional nanoparticles. Small. Jun. 10, 2013;9(11):1964-73. doi: 10.1002/smll.201201973. Epub Jan. 6, 2013.
Houot et al., T-cell modulation combined with intratumoral CpG cures lymphoma in a mouse model without the need for chemotherapy. Blood. Apr. 9, 2009;113(15):3546-52. doi: 10.1182/blood-2008-07-170274. Epub Oct. 21, 2008.
Kim et al., Cationic solid lipid nanoparticles reconstituted from low density lipoprotein components for delivery of siRNA. Mol Pharm. Jul.-Aug. 2008;5(4):622-31. doi: 10.1021/mp8000233. Epub May 8, 2008.
Kong et al., Cationic lipid-coated gold nanoparticles as efficient and non-cytotoxic intracellular siRNA delivery vehicles. Pharm Res. Feb. 2012;29(2):362-74. doi: 10.1007/s11095-011-0554-y. Epub Aug. 13, 2011.
Polizzi et al., Water-soluble nitric oxide-releasing gold nanoparticles. Langmuir. Apr. 24, 2007;23(9):4938-43. Epub Mar. 22, 2007.
Radovic-Moreno et al., Immunomodulatory spherical nucleic acids. Proc Natl Acad Sci U S A. Mar. 31, 2015;112(13):3892-7. doi: 10.1073/pnas.1502850112. Epub Mar. 16, 2015.
Rothrock et al., Synthesis of nitric oxide-releasing gold nanoparticles. J Am Chem Soc. Jul. 6, 2005;127(26):9362-3.
Saraiva et al., Nanocarriers for nitric oxide delivery. J Drug Deliv. 2011;2011:936438. doi: 10.1155/2011/936438. Epub Aug. 22, 2011.
Wu et al., DNA aptamer-micelle as an efficient detection/delivery vehicle toward cancer cells. Proc Natl Acad Sci U S A. Jan. 5, 2010;107(1):5-10. doi: 10.1073/pnas.0909611107. Epub Dec. 22, 2009.
International Search Report and Written Opinion for Application No. PCT/US2017/051930, dated Nov. 22, 2017.

[No Author Listed], Aurasense Therapeutics NIH Grant. Topically-Delivered Targeted Gene Suppression of Immune Activation in Psoriasis. https://projectreporter.nih.gov/pr_Pij_info_desc_dtls.cfm?icde=0&aid=8710888&print=yes Last accessed Dec. 12, 2017.
Khmelinskaia et al., Effect of anchor positioning on binding and diffusion of elongated 3D DNA nanostructures on lipid membranes. J. Phys. D: Appl. Phys. Apr. 13, 2013;49(19):194001.
Palekar et al., Nanoparticle-based biosensors for the detection of lecithin: cholesterol acyltransferase activity. The FASEB Journal 31(1), 2017. 2 pages.
Banga et al., Liposomal spherical nucleic acids. J Am Chem Soc. Jul. 16, 2014;136(28):9866-9. doi: 10.1021/ja504845f. Epub Jul. 1, 2014.
Briley et al., In Nanomaterials for Biomedicine; American Chemical Society. 2012;1119:1-20.
Choi et al., Mechanism for the endocytosis of spherical nucleic acid nanoparticle conjugates, Proc. Natl. Acad. Sci. U.S.A. 2013;110:7625-7630.
Cutler et al., Spherical nucleic acids. J Am Chem Soc. Jan. 25, 2012;134(3):1376-91. doi: 10.1021/ja209351u. Epub Jan. 9, 2012.
Kelly et al., Targeted Liposomal Drug Delivery to Monocytes and Macrophages. J Drug Delivery. 2011;1-11.
Kim et al., Effect of bovine serum albumin on the stability of methotrexate-encapsulated liposomes, Arch. Pharmacal Res. 1991;14:336.
Lee et al., Imageable antigen-presenting gold nanoparticle vaccines for effective cancer immunotherapy in vivo. Angew Chem Int Ed Engl. Aug. 27, 2012;51(35):8800-5. doi:10.1002/anie.201203193.
Marquele-Oliveira et al., Development of nitrosyl ruthenium complex-loaded lipid carriers for topical administration: improvement in skin stability and in nitric oxide release by visible light irradiation. J Pharm Biomed Anal. Dec. 1, 2010;53(4):843-51. doi: 10.1016/j.jpba.2010.06.007. Epub Jun. 19, 2010.
Pearson et al., Polynucleotide Binding to Macrophage Scavenger Receptors Depends on the Formation of Base-quartet-stabilized Four-stranded Helices. JBC, VOi. 268, No. 5, Issue Of Feb. 15. pp. 3546-3554, 1993 (Year: 1993).
Thompson et al., Smart lipids for programmable nanomaterials. Nano Lett. Jul. 14, 2010;10(7):2690-3. doi: 10.1021/nl101640k.
Zhang et al., Informational liposomes: Complexes derived from cholesteryl-conjugated oligonucleotides and liposomes. Tetrahedron Letters. 1996. 37(35):6243-6.
Zheng et al., A spherical nucleic acid platform based on self-assembled DNA biopolymer for high-performance cancer therapy. ACS Nano. Aug. 27, 2013;7(8):6545-54. doi: n402344v. Epub Jul. 23, 2013.
Zheng et al., Topical delivery of siRNA-based spherical nucleic acid nanoparticle conjugates for gene regulation. Proc Natl Acad Sci U S A. Jul. 24, 2012;109(30):11975-80. doi: 10.1073/pnas.1118425109. Epub Jul. 6, 2012.

\* cited by examiner c d

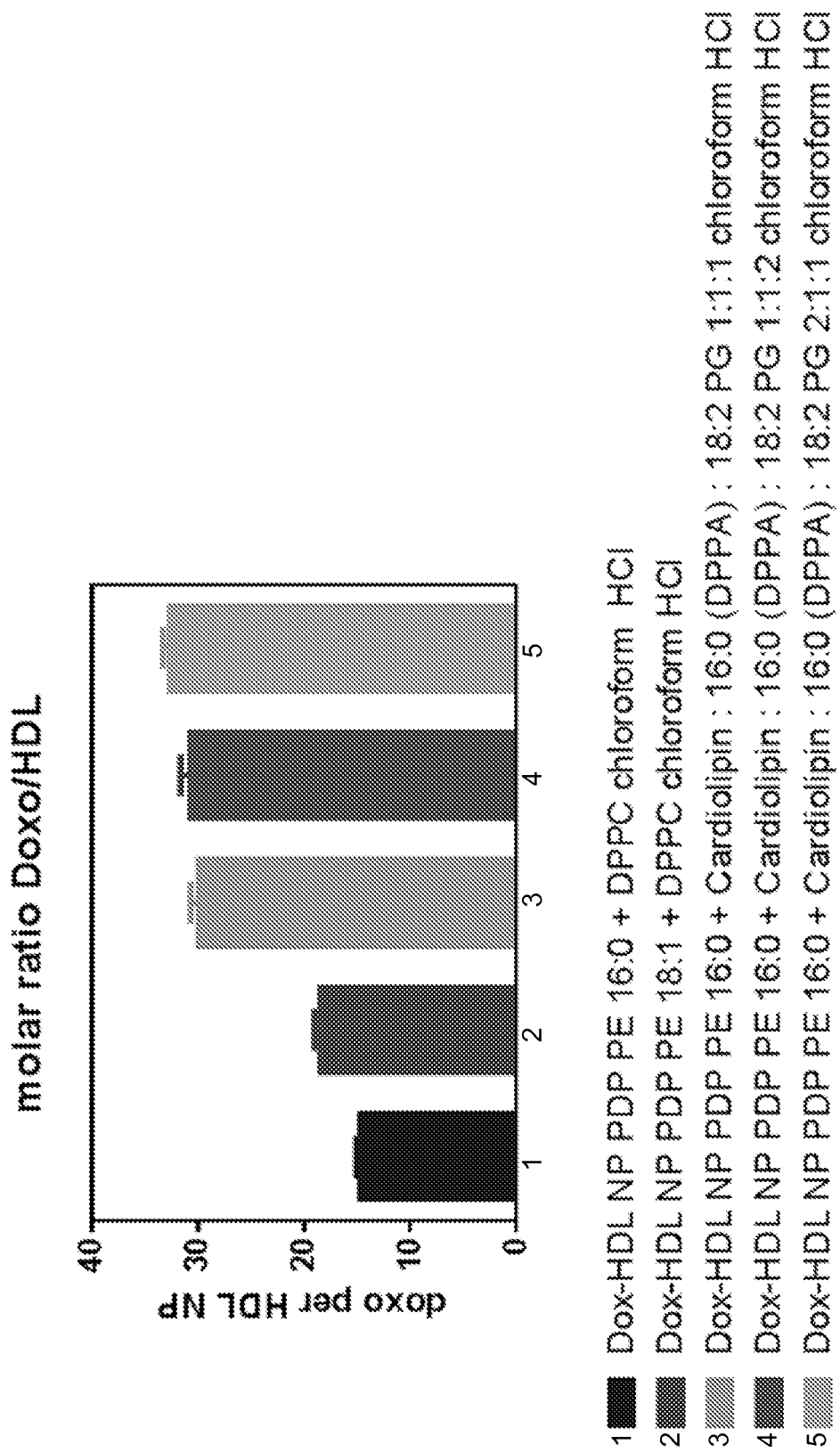

LIPOPHILIC NANOPARTICLES FOR DRUG DELIVERY

RELATED APPLICATIONS

This application claims priority under 35 U.S.C. § 119(e) to U.S. Provisional Application Ser. No. 61/865,551, entitled "LIPOPHILIC NANOPARTICLES FOR DRUG DELIVERY" filed on Aug. 13, 2013, which is herein incorporated by reference in its entirety.

BACKGROUND OF THE INVENTION

After years of advances in cancer therapy, cancer remains a difficult disease to treat. Existing chemotherapeutic remedies have nonspecific toxicity, poor solubility, and multiple-drug resistance. Conventional cancer chemotherapeutic agents target the metabolic and structural machinery needed by rapidly dividing cells to maintain growth. These structurally heterogeneous agents function through a variety of mechanisms, including intercalating within the DNA of rapidly dividing cells, interrupting microtubule function, and crosslinking DNA via alkylation. However, one of the major limitations of conventional cancer therapeutics is dose-limiting side effects, largely from drug effect in non-targeted tissues.

SUMMARY OF THE INVENTION

The invention in some aspects is a structure having a nanostructure core comprising an inorganic material; a shell comprising a lipid layer surrounding and attached to the nanostructure core, the shell having an inner surface and an outer surface, wherein the shell has a therapeutic profile for a therapeutic agent; wherein the therapeutic agent is attached to the shell, and a protein bound to at least the outer surface of the shell. In some embodiments the protein is an apolipoprotein.

The invention in other aspects is a structure having a nanostructure core comprising an inorganic material; a shell comprising a lipid layer surrounding and attached to the nanostructure core, the shell having an inner surface and an outer surface; an apolipoprotein bound to at least the outer surface of the shell and a therapeutic agent adsorbed on the outer shell and/or incorporated between the inner surface and outer surface of the shell, wherein the therapeutic agent is chosen from the group consisting of doxorubicin, andrographolide, and vincristine.

In other embodiments the therapeutic profile is associated with the outer surface of the shell. In yet other embodiments the therapeutic profile is lipids in the outer surface of the shell having negative head groups.

At least 80%, 85%, 90%, 95%, 98% 99% or 100% of the lipids in the outer surface of the shell have negatively charged head groups in some embodiments.

At least 80%, 85%, 90%, 95%, 98% 99% or 100% of the lipids in the outer surface of the shell have positively charged head groups in some embodiments.

In some embodiments at least 80%, 85%, 90%, 95%, 98% 99% or 100% of the lipids in the outer surface of the shell have neutral positively charged head groups. In other embodiments the therapeutic profile is lipids in the outer surface of the shell having mixtures of negative and neutral head groups, mixtures of positive and neutral head groups, mixtures of negative and positive head groups, or mixtures of negative, positive and neutral head groups. In other embodiments the shell comprises lipids and the lipids in the shell are selected from the group consisting of phospholipids, unsaturated lipids, saturated lipids, and therapeutic lipids.

The lipids in the shell in some embodiments are comprised of 18:0 (DSPG), 16:0 PG, 18:1 delta9-Cis PG, 18:3 PG, 18:0 PA (DSPA), cardiolipin, brain PI, 16:0 PA, and 18:2 PG.

The shell is associated with cholesterol, Poly(styrenesulfonate) or a nucleic acid having a doxorubicin binding motif incorporated therein such as DNA in some embodiments.

The therapeutic agent in some embodiments is chosen from the group consisting of doxorubicin, andrographolide, and vincristine.

In embodiments the structure includes 20-40 therapeutic agents per structure. The 20-40 therapeutic agents may be one type of therapeutic agent or the 20-40 therapeutic agents may be at least two types of therapeutic agents. In some embodiments the structure includes a number of therapeutic agents per structure selected from a range consisting of 1-20, 20-40, 40-60, 60-80, 80-100, 20-100, 20-200, 20-300, 20-400, 20-500, 20-600, 20-700, 20-800, 20-900.

Peptides or peptidomimetics are attached to proteins of the shell through alkylation of their lysine residues in some embodiments. The peptide or peptidomimetic may bind to a cell surface receptor.

In some embodiments the therapeutic profile is unsaturated fatty in the shell.

In other aspects the invention is a structure having a nanostructure core comprising an inorganic material; a shell comprising a lipid layer surrounding and attached to the nanostructure core, the shell having an inner surface and an outer surface, and a therapeutic agent associated with the shell, wherein 20-40 therapeutic agents are associated per structure. In some embodiments a protein such as an apolipoprotein is also associated with the shell. In some embodiments 30-40 therapeutic agents are associated per structure.

A method of treating cancer with reduced cardiotoxicity by administering to a subject having cancer a nanostructure comprising a core, a shell comprising a lipid layer surrounding and attached to the core, the shell having an inner surface and an outer surface; an apolipoprotein associated with the shell and a chemotherapeutic agent having cardiotoxic properties in order to treat the cancer, while causing less cardiotoxicity than the cardiotoxicity caused by treatment of a subject having cancer with the chemotherapeutic agent alone is provided according to other aspects of the invention.

In another aspect the invention is a method of treating cancer, by administering to a subject having cancer a nanostructure having a core, a lipid layer on the exterior of the core, a protein, and a chemotherapeutic agent, wherein the nanostructure is administered at a sub-therapeutic dosage for the chemotherapeutic agent alone.

According to yet another aspect, the invention is a method for delivering a therapeutic agent to a subject, by administering to a subject a structure as described herein in an effective amount to deliver the therapeutic agent to the subject.

In some embodiments the nanostructure is administered at a dosage that is 100 fold lower concentration than a therapeutic dosage of the chemotherapeutic agent for the cancer. In another embodiment the nanostructure is administered at a dosage that is 250 fold lower concentration than a therapeutic dosage of the chemotherapeutic agent for the cancer. In yet other embodiments at least 20 therapeutic or chemotherapeutic agents are bound per structure.

In other aspects of the invention a method of treating a disease with reduced toxicity, by administering to a subject having a disease a nanostructure comprising a core, a shell comprising a lipid layer surrounding and attached to the core, the shell having an inner surface and an outer surface; an apolipoprotein associated with the shell and a therapeutic agent having toxic properties in order to treat the disease, while causing less toxicity than the toxicity caused by treatment of a subject having the disease with the therapeutic agent alone is provided. In some embodiments the toxicity is cardiotoxicity, liver, neurological, bone marrow, intestinal, dermatologic, pulmonary, or kidney toxicity.

In yet other aspects the invention is a method of treating disease by administering to a subject having a disease a nanostructure having a core, a lipid layer on the exterior of the core, a protein, and a therapeutic agent, wherein the nanostructure is administered at a sub-therapeutic dosage for the therapeutic agent alone. In some embodiments the disease is immunological disease, vascular disease, rheumatologic disease, or infectious disease. In other embodiments the therapeutic agent is selected from an anti-cancer agent, an anti-immunological disease agent, an anti-vascular disease agent, or an anti-rheumatologic disease agent.

In any of the above described embodiments the lipid layer is a lipid monolayer or a lipid bilayer.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. The details of one or more embodiments of the invention are set forth in the accompanying Detailed Description, Examples, Claims, and Figures. Other features, objects, and advantages of the invention will be apparent from the description and from the claims.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2A shows zeta-potential of particles change in accordance with addition of charged functionalities (apolipoprotein, phospholipids). Significant changes in zeta-potential are observed upon addition of doxorubicin (doxB) and andrographolide (AndroA and AndroB) compared to the bare HDL NPs (HDL-AuNP). Hydrodynamic radius is observed to increase slightly with addition of ApoA1 Au+ApoA1), as shown in FIG. 2B, and greatly with addition of phospholipid bilayer, but does not change significantly upon addition of the small drug molecules (Dox and Andro).

FIG. 4E and FIG. 4F show HDL-Doxorubicin NPs in Jurkat cells.

FIG. 8A depicts the absorbance spectra of HDL-NP and Dox-HDL-NP, which display a characteristic surface plasmon band (SPB) at approximately 520 nm. FIG. 8B shows that the zeta-potential of particles changes in accordance with addition of charged functionalities (apolipoprotein, phospholipids). Significant changes in zeta-potential are also observed upon addition of doxorubicin. FIG. 8C shows that the hydrodynamic radius of the gold particle increases slightly with addition of ApoA1, and greatly with addition of phospholipid. Additional inclusion of doxorubicin in the synthesis does not alter the radius significantly compared to bare HDL NP, presumably due to the small size of the drug compared to the HDL NP. FIG. 8D demonstrates that doxorubicin fluorescence (ex=490 nm) is largely quenched in the Dox-HDL-NP under neutral (binding) conditions due to its close proximity to the gold core. Drug fluorescence is restored by treatment with 0.2 M HCl. HDL-NPs without drug are not fluorescent. FIG. 8E shows that doxorubicin fluorescence is quenched upon addition of increasing concentrations of HDL-NP. FIG. 8F illustrates the increasing fluorescence anisotropy of doxorubicin is bound to the HDL-NP under neutral conditions. Acid-treatment of Dox-HDL-NP releases the drug and restores florescence anisotropy to the value observed for free doxorubicin in 0.2 M HCl or in water.

In FIG. 9A, a doxorubicin standard curve is shown. FIG. 9B shows the doxorubicin standard curve, which is used to assess how much doxorubicin is released by a given amount of Dox-HDL-NP in 0.2 M HCl as compared to Dox-HDL-NP in water. The same amount of bare HDL-NP is included in the standard curve.

FIG. 13A demonstrates that loaded doxorubicin per HDL-NP increases linearly across the range of synthesis stoichiometries measured. Dox-HDL-NP show substantial improvements in cytotoxic efficiency compared to HDL-NPs and free doxorubicin in Ramos (FIG. 13B) and SUDHL4 (FIG. 13C) cells after 48 hours. Survival was adjusted to cells treated with PBS instead of drug/NP (100% survival) and to medium treated with PBS (0% survival).

FIG. 20 shows the number of doxorubicin molecules bound per HDL NP after purification, which was determined by denaturing the different Dox-HDL NPs through addition of acid and determining the amount of released doxorubicin utilizing the intrinsic fluorescence of doxorubicin.

DETAILED DESCRIPTION OF THE INVENTION

Figure 1:
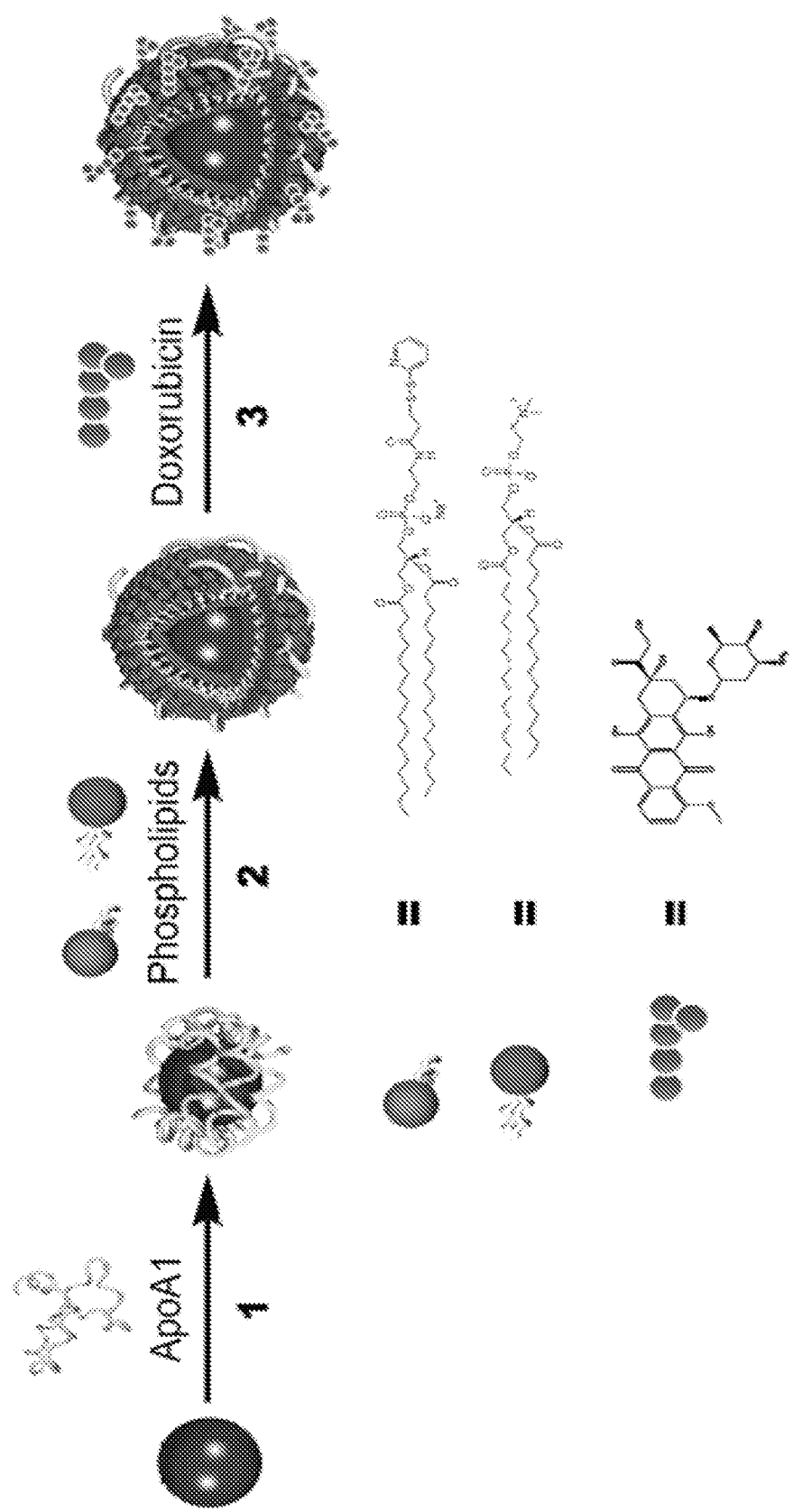
FIG. 1 depicts an exemplary HDL-Drug NP (nanostructure) assembly scheme. (1) colloidal gold is functionalized with the protein component, ApoA1. (2) ApoA1-gold complex is decorated with phospholipids (i.e., DIS and DPPC), along with (3) the drug i.e., doxorubicin.

Novel methods of drug delivery are necessary to overcome issues with existing chemotherapeutic remedies, including nonspecific toxicity, poor solubility, and multiple-drug resistance. The invention described herein is a versatile platform for targeted delivery of lipophilic and amphipathic drugs, based on synthetic high-density lipoprotein nanoparticles (HDL-NPs). Nanostructures are synthesized using an inorganic nanoparticle core, such as a gold core, to control size and shape, and can be co-incubated with a variety of different therapeutic agents. Nanostructures loaded with several therapeutic agents, including the common chemotherapeutic doxorubicin, were characterized by size, surface charge, UV absorbance, and fluorescence. The data is presented below in the Examples section.

The nanostructures described herein function in several ways. For example the nanoparticles are able to mimic the interaction between natural HDL and the scavenger receptor type B-1 (SR-B1), conferring specificity for the nanostructures to cells expressing this receptor—notably lymphomas, prostate cancer, and breast cancer cells. An advantage of this finding is that cytotoxicity is shown to be higher in lymphoma and epithelial malignancies than towards cardiomyoblasts. Substantially improved killing efficiency is observed in lymphoma for the drug-loaded nanoparticles (i.e. HDL-NPs) compared to either bare HDL-NPs or the free drug in solution, suggests a synergistic killing effect. Formulation of nanoparticles containing several drugs demonstrates the versatility of this approach and its applicability to a wide variety of cancers and other diseases.

Conventional drug delivery strategies struggle to balance the need for high local concentrations of a drug at the site of interest against the danger of toxicity of the drug at high concentrations elsewhere. This problem is particularly challenging in chemotherapy, where nonspecific drugs are delivered at high doses to kill cancer cells, but severe and undesirable side effects result from interactions with non-cancerous cells in the rest of the body. Additionally, some drugs cannot be readily formulated because they are insoluble in water. The nanoparticles of the invention overcome prior art problems, leading to effective therapies with reduced side effects and capable of actively targeting cells of interest (e.g. tumor cells).

High-density lipoproteins (HDL) are naturally-occurring nanoparticles that assemble dynamically in serum from phospholipids, apolipoproteins, and cholesterol. HDL is involved in reverse-cholesterol transport, and has been epidemiologically correlated with reduced incidences of cardiovascular disease.[3,4] Natural HDL is known to bind Scavenger Receptor type B-1 (SR-B1); SR-B1 mediates uptake of cholesteryl esters and the uptake and efflux free cholesterol. Cholesterol uptake has been shown to be critical for proliferation of several types of cancers, including lymphoma, prostate cancer, and breast cancer.

Previous studies have demonstrated that synthetic HDL NPs significantly inhibit growth of B-cell lymphomas through a combination of SR-B1 binding (and downstream signaling events), as well as cholesterol starvation.[5] The findings of the invention presents a novel platform for formulating and delivering, in a targeted manner, lipophilic and amphipathic drugs to a variety of cells. Specifically, the loading of the chemotherapeutics onto gold-templated synthetic high-density lipoprotein nanoparticles (HDL NPs) is demonstrated and characterized. Doxorubicin is widely used as part of several chemotherapy regimes (ABVD,[21] BEA-COPP, CHOP,[22] etc.) to treat various cancers, but its administration is limited by doxorubicin's high cardiotoxicity, constraining its uses to those cancers where it is effective at low doses.

The killing efficiency is shown to be higher for the drug-loaded nanoparticles (HDL-Drug NPs) in this study than either the "bare" HDL-NPs (those without drugs) or the free drug in solution. These results suggest it may be possible to administer doxorubicin and other therapeutic agents at much lower doses and achieve comparable clinical effectiveness. Further, the nanoparticles are believed to act via a specific receptor-mediated pathway, limiting effects to those cells expressing the receptor.

Thus, in some aspects the invention is a nanostructure composed of a nanostructure core of an inorganic material surrounded by a shell of a lipid layer, and a therapeutic agent associated with the shell. The nanostructure may also include a protein such as an apolipoprotein.

The shell may have an inner surface and an outer surface, such that the therapeutic agent and/or the apolipoprotein may be adsorbed on the outer shell and/or incorporated between the inner surface and outer surface of the shell.

The shell may also have a therapeutic profile for a therapeutic agent. A "therapeutic profile" as used herein refers to a composition of lipids and/or proteins that promote binding of a particular therapeutic agent. Each therapeutic agent has a particular shape, charge, and degree or level of hydrophobicity that may contribute to its ability to bind to the shell and or protein bound to the surface The binding capacity as well as binding affinity between the therapeutic agent and the nanostructure may be regulated by modification to the therapeutic profile. For instance, a particular combination of lipids may provide an optimal surface for binding to a small molecule or protein. Positively charged head groups in the outer layer are shown to decrease the binding affinity, while negatively charged lipid head groups increase the binding affinity.

Examples of nanostructures that can be used in the methods are described herein are now described. The structure (e.g., a synthetic structure or synthetic nanostructure) has a core and a shell surrounding the core. In embodiments in which the core is a nanostructure, the core includes a surface to which one or more components can be optionally attached. For instance, in some cases, core is a nanostructure surrounded by shell, which includes an inner surface and an outer surface. The shell may be formed, at least in part, of one or more components, such as a plurality of lipids, which may optionally associate with one another and/or with surface of the core. For example, components may be associated with the core by being covalently attached to the core, physiosorbed, chemisorbed, or attached to the core through ionic interactions, hydrophobic and/or hydrophilic interactions, electrostatic interactions, van der Waals interactions, or combinations thereof. In one particular embodiment, the core includes a gold nanostructure and the shell is attached to the core through a gold-thiol bond.

The nanostructures of the invention include a therapeutic agent. A therapeutic agent is any active agent useful in treating or preventing a disease in a subject. In some instances the therapeutic agent is a chemotherapeutic agent. Chemotherapeutic agents include but are not limited to methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS famesyl transferase inhibitor, famesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Placlitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methylGAG; methyl glyoxal bis-guanylhydrazone; MGBG), Pentostatin (2'deoxycoformycin), Semustine (methyl-CCNU), Teniposide (VM-26) and Vindesine sulfate. In an important embodiment, the cancer medicament is taxol.

The therapeutic agent may also be another type of anti-cancer agent (a non-chemotherapeutic agent, an anti-immunological disease agent, an anti-vascular disease agent, or an anti-rheumatologic disease agent. Anti-cancer agents include immunotherapeutic agents, cancer vaccines, biological response modifiers (e.g., cytokines and hemopoietic growth factors), or hormone therapies (e.g., adrenocorticosteroids, androgens, anti-androgens, estrogens, anti-estrogens, progestins, aromatase inhibitor, gonadotropin-releasing hormone agonists, and somatostatin analogs).

The cancer medicament may be an immunotherapeutic agent selected from the group consisting of Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab and ImmuRAIT-CEA.

In yet another embodiment, the cancer medicament is a cancer vaccine selected from the group consisting of EGF, Anti-idiotypic cancer vaccines, Gp75 antigen, GMK melanoma vaccine, MGV ganglioside conjugate vaccine, Her2/neu, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVA-based vaccine, PACIS, BCG vaccine, TA-HPV, TA-CIN, DISC-virus and ImmuCyst/TheraCys.

In still another embodiment, the cancer medicament is a hormone therapy. In a related embodiment, the hormone therapy is selected from the group consisting of estrogen therapy e.g., diethylstilbestrol and ethinyl estradiol, anti-estrogen therapy e.g., tamoxifen, progestin therapy e.g., medroxyprogesterone and megestrol acetate, androgen blockade e.g., anti-androgens such as flutamide, adrenocorticosteroids including adrenal steroids, synthetic glucocorticoid therapy e.g., prednisone, methylprednisone, and dexamethasone, androgens e.g., fluoxymesterone, synthetic testosterone analogs, aromatase inhibitor e.g., aminoglutethimide, gonadotropin-releasing hormone agonists e.g., leuprolide, somatostatin analogs e.g., octreotide.

The anti-infectious disease agent may be an anti-bacterial agent, an anti-fungal agent an anti-parasitic agent or an anti-viral agent. Anti-bacterial agents include but are not limited to natural penicillins, semi-synthetic penicillins, clavulanic acid, cephalolsporins, bacitracin, ampicillin, carbenicillin, oxacillin, azlocillin, mezlocillin, piperacillin, methicillin, dicloxacillin, nafcillin, cephalothin, cephapirin, cephalexin, cefamandole, cefaclor, cefazolin, cefuroxine, cefoxitin, cefotaxime, cefsulodin, cefetamet, cefixime, ceftriaxone, cefoperazone, ceftazidine, moxalactam, carbapenems, imipenems, monobactems, eurtreonam, vancomycin, polymyxin, amphotericin B, nystatin, imidazoles, clotrimazole, miconazole, ketoconazole, itraconazole, fluconazole, rifampins, ethambutol, tetracyclines, chloramphenicol, macrolides, aminoglycosides, streptomycin, kanamycin, tobramycin, amikacin, gentamicin, tetracycline, minocycline, doxycycline, chlortetracycline, erythromycin, roxithromycin, clarithromycin, oleandomycin, azithromycin, chloramphenicol, quinolones, co-trimoxazole, norfloxacin, ciprofloxacin, enoxacin, nalidixic acid, temafloxacin, sulfonamides, gantrisin, and trimethoprim, Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; and Zorbamycin.

The anti-fungal agent may include Acrisorcin; Ambruticin; Amorolfine, Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofungin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafungin; Undecylenic Acid; Viridofulvin; Zinc Undecylenate; and Zinoconazole Hydrochloride imidazoles, FK 463, amphotericin B, BAY 38-9502, MK 991, pradimicin, UK 292, butenafine, chitinase and 501 cream.

The antiviral agent in some embodiments is Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; or Zinviroxime.

A number of therapeutic agents are typically associated with the shell of a nanostructure. For instance, at least 20 therapeutic agents may be associated per structure. In general at least 20-30, 20-40, 20-50, 25-30, 25-40, 25-50, 30-40, 30-50, 35-40, 35-50, 40-45, 40-50, 45-50, 50-100 or 30-100 20 therapeutic agents may be associated per structure.

Doxorubicin, an anthracycline antibiotic, widely used in several cancer chemotherapy regimens has been demonstrated herein to be effectively delivered using the nanostructures of the invention. Doxorubicin is used to treat leukemia, Hodgkin's lymphoma, and breast cancer (among others). Administration of Doxorubicin is generally limited by its severe cardiac toxicity.[9-11] Doxorubicin has been delivered in liposomes, as well as pH-responsive micelles.[12-14] Doxorubicin has also been formulated on several polymeric nanoparticles.[15-18] The nanostructures herein, have the surprising and advantageous property of reduced cardiotoxicity.

Optionally, components can be crosslinked to one another. Crosslinking of components of a shell can, for example, allow the control of transport of species into the shell, or between an area exterior to the shell and an area interior of the shell. For example, relatively high amounts of crosslinking may allow certain small, but not large, molecules to pass into or through the shell, whereas relatively low or no crosslinking can allow larger molecules to pass into or through the shell. Additionally, the components forming the shell may be in the form of a monolayer or a multilayer, which can also facilitate or impede the transport or sequestering of molecules. In one exemplary embodiment, shell includes a lipid bilayer that is arranged to sequester cholesterol and/or control cholesterol efflux out of cells, as described herein.

It should be understood that a shell which surrounds a core need not completely surround the core, although such embodiments may be possible. For example, the shell may surround at least 50%, at least 60%, at least 70%, at least 80%, at least 90%, or at least 99% of the surface area of a core. In some cases, the shell substantially surrounds a core. In other cases, the shell completely surrounds a core. The components of the shell may be distributed evenly across a surface of the core in some cases, and unevenly in other cases. For example, the shell may include portions (e.g., holes) that do not include any material in some cases. If desired, the shell may be designed to allow penetration and/or transport of certain molecules and components into or out of the shell, but may prevent penetration and/or transport of other molecules and components into or out of the shell. The ability of certain molecules to penetrate and/or be transported into and/or across a shell may depend on, for example, the packing density of the components forming the shell and the chemical and physical properties of the components forming the shell. The shell may include one layer of material, or multilayers of materials in some embodiments.

The core of the nanostructure whether being a nanostructure core or a hollow core, may have any suitable shape and/or size. For instance, the core may be substantially spherical, non-spherical, oval, rod-shaped, pyramidal, cube-like, disk-shaped, wire-like, or irregularly shaped. The core (e.g., a nanostructure core or a hollow core) may have a largest cross-sectional dimension (or, sometimes, a smallest cross-section dimension) of, for example, less than or equal to about 500 nm, less than or equal to about 250 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. In some cases, the core has an aspect ratio of greater than about 1:1, greater than 3:1, or greater than 5:1. As used herein, "aspect ratio" refers to the ratio of a length to a width, where length and width measured perpendicular to one another, and the length refers to the longest linearly measured dimension.

The core may be formed of an inorganic material. The inorganic material may include, for example, a metal (e.g., Ag, Au, Pt, Fe, Cr, Co, Ni, Cu, Zn, and other transition metals), a semiconductor (e.g., silicon, silicon compounds and alloys, cadmium selenide, cadmium sulfide, indium arsenide, and indium phosphide), or an insulator (e.g., ceramics such as silicon oxide). The inorganic material may be present in the core in any suitable amount, e.g., at least 1 wt %, 5 wt %, 10 wt %, 25 wt %, 50 wt %, 75 wt %, 90 wt %, or 99 wt %. In one embodiment, the core is formed of 100 wt % inorganic material. The nanostructure core may, in some cases, be in the form of a quantum dot, a carbon nanotube, a carbon nanowire, or a carbon nanorod. In some cases, the nanostructure core comprises, or is formed of, a material that is not of biological origin. In some embodiments, a nanostructure includes or may be formed of one or more organic materials such as a synthetic polymer and/or a natural polymer. Examples of synthetic polymers include non-degradable polymers such as polymethacrylate and degradable polymers such as polylactic acid, polyglycolic acid and copolymers thereof. Examples of natural polymers include hyaluronic acid, chitosan, and collagen.

Furthermore, a shell of a structure can have any suitable thickness. For example, the thickness of a shell may be at least 10 Angstroms, at least 0.1 nm, at least 1 nm, at least 2 nm, at least 5 nm, at least 7 nm, at least 10 nm, at least 15 nm, at least 20 nm, at least 30 nm, at least 50 nm, at least 100 nm, or at least 200 nm (e.g., from the inner surface to the outer surface of the shell). In some cases, the thickness of a shell is less than 200 nm, less than 100 nm, less than 50 nm, less than 30 nm, less than 20 nm, less than 15 nm, less than 10 nm, less than 7 nm, less than 5 nm, less than 3 nm, less than 2 nm, or less than 1 nm (e.g., from the inner surface to the outer surface of the shell). Such thicknesses may be determined prior to or after sequestration of molecules as described herein.

The shell of a structure described herein may comprise any suitable material, such as a hydrophobic material, a hydrophilic material, and/or an amphiphilic material. Although the shell may include one or more inorganic materials such as those listed above for the nanostructure core, in many embodiments the shell includes an organic material such as a lipid or certain polymers. The components of the shell may be chosen, in some embodiments, to facilitate the binding capacity as well as binding affinity of the therapeutic agent. For example, positively charged head groups in the outer layer can decrease the binding affinity of a therapeutic agent such as doxorubicin, while negatively charged lipid head groups increase the binding affinity of doxorubicin. Changes in the lipid composition of the nanoparticle can not only change the binding affinity between therapeutic agent and the nanostructure, but also the binding capacity of the nanostructure for therapeutic agent. The binding affinity of the nanoparticles may be further altered by including cholesterol (the modulate fluidity of the lipid layer), Poly(styrenesulfonate) (negatively charged polymer for enhanced doxorubicin binding) or DNA (with a doxorubicin binding motif) in the synthesis step.

The nanostructures described herein are unique and combine several distinct advantages compared to prior art nanostructures that have been used to formulate anti-cancer drugs such as doxorubicin.

For instance, the nanostructures of the invention have intrinsic cytotoxic effect. The cytotoxicity of the nanostructures is mediated through SR-B1, a cell surface receptor that interacts with both natural HDL and HDL-NPs. This interaction leads to decreased cholesterol transport by SR-B1, starving the cell of an essential molecule needed for cell division and growth. Furthermore, as a biomimic of HDL, the nanostructures have inherent targeting specificity to cells expressing the SR-B1 receptor. This targeting specificity for the SR-B1 receptor is conferred by both the size of the nanostructure and the presence of the ApoA1 protein—a ligand for SR-B1—on the surface of the nanostructure.

Another distinction between the nanostructures described herein and other reported formulations for doxorubicin is that the nanostructures of the invention are small, with a diameter of approximately 13 nm. Increasing evidence suggests that the ability of a nanostructure to avoid endolysosomal sequestration and thus deliver a therapeutic payload to a bioavailable intracellular location is strongly determined by the size of the nanostructure. The subcellular localization of these nanostructures in the cytoplasm. Herein we show confocal microscopy evidence demonstrating that the doxorubicin is ultimately delivered to the nucleus, its major site of action.

Third, this formulation of anticancer drugs has enhanced potency compared to unformulated drugs owing to the intrinsic killing effect of the HDL-NP platform. This enhanced potency is in part due to the high loading efficiency of small molecule drug on the nanoparticle. As demonstrated herein, the nanostructures enable the use of chemotherapeutic agents in treating a broader spectrum of cancer than current usage allows. For instance, the formulation of doxorubicin can be used in the treatment of cancer in addition to lymphomas, such as breast and prostate cancer.

As discussed above, by changing the lipid composition of the outer leaflet of the nanostructures for example, this micro-environment could easily be adjusted to bind doxorubicin and different drugs with optimal affinity. Keeping the outer lipid sufficiently fluent by using unsaturated fatty acids may allow more hydrophobic drugs to intercalate into the lipid layer. This is important, since many compounds that could be used as anti-cancer drugs show low solubility in water due to their hydrophobic nature and have been dropped from the drug development pipeline for this reason. However, even highly charged small molecules could associate with the nanostructures when using phospholipids with favorably charged head groups. The protein composition of the nanostructures can also be modified to optimized small molecule binding. For example it has been shown that peptides and peptidomimetics can be attached to apoproteins through alkylation of their lysine residues to target the lipo particle to a variety of different receptors.

In one set of embodiments, a structure described herein or a portion thereof, such as a shell of a structure, includes one or more natural or synthetic lipids or lipid analogs (i.e., lipophilic molecules). One or more lipids and/or lipid analogues may form a single layer or a multi-layer (e.g., a bilayer) of a structure. In some instances where multi-layers are formed, the natural or synthetic lipids or lipid analogs interdigitate (e.g., between different layers). Non-limiting examples of natural or synthetic lipids or lipid analogs include fatty acyls, glycerolipids, glycerophospholipids, sphingolipids, saccharolipids and polyketides (derived from condensation of ketoacyl subunits), and sterol lipids and prenol lipids (derived from condensation of isoprene subunits).

In one particular set of embodiments, a structure described herein includes one or more phospholipids. The one or more phospholipids may include, for example, phosphatidylcholine, phosphatidylglycerol, lecithin, β, γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, 1,2-dipalmitoyl-sn-glycero-3-phosphothioethanol, and combinations thereof. In some cases, a shell (e.g., a bilayer) of a structure includes 50-200 natural or synthetic lipids or lipid analogs (e.g., phospholipids). For example, the shell may include less than about 500, less than about 400, less than about 300, less than about 200, or less than about 100 natural or synthetic lipids or lipid analogs (e.g., phospholipids), e.g., depending on the size of the structure.

Non-phosphorus containing lipids may also be used such as stearylamine, docecylamine, acetyl palmitate, and fatty acid amides. In other embodiments, other lipids such as fats, oils, waxes, cholesterol, sterols, fat-soluble vitamins (e.g., vitamins A, D, E and K), glycerides (e.g., monoglycerides, diglycerides, triglycerides) can be used to form portions of a structure described herein.

A portion of a structure described herein such as a shell or a surface of a nanostructure may optionally include one or more alkyl groups, e.g., an alkane-, alkene-, or alkyne-containing species, that optionally imparts hydrophobicity to the structure. An "alkyl" group refers to a saturated aliphatic group, including a straight-chain alkyl group, branched-chain alkyl group, cycloalkyl (alicyclic) group, alkyl substituted cycloalkyl group, and cycloalkyl substituted alkyl group. The alkyl group may have various carbon numbers, e.g., between C2 and C40, and in some embodiments may be greater than C5, C10, C15, C20, C25, C30, or C35. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., C1-C12 for straight chain, C3-C12 for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclochexyl, and the like.

The alkyl group may include any suitable end group, e.g., a thiol group, an amino group (e.g., an unsubstituted or substituted amine), an amide group, an imine group, a carboxyl group, or a sulfate group, which may, for example, allow attachment of a ligand to a nanostructure core directly or via a linker. For example, where inert metals are used to form a nanostructure core, the alkyl species may include a thiol group to form a metal-thiol bond. In some instances, the alkyl species includes at least a second end group. For example, the species may be bound to a hydrophilic moiety such as polyethylene glycol. In other embodiments, the second end group may be a reactive group that can covalently attach to another functional group. In some instances, the second end group can participate in a ligand/receptor interaction (e.g., biotin/streptavidin).

In some embodiments, the shell includes a polymer. For example, an amphiphilic polymer may be used. The polymer may be a diblock copolymer, a triblock copolymer, etc., e.g., where one block is a hydrophobic polymer and another block is a hydrophilic polymer. For example, the polymer may be a copolymer of an α-hydroxy acid (e.g., lactic acid) and polyethylene glycol. In some cases, a shell includes a hydrophobic polymer, such as polymers that may include certain acrylics, amides and imides, carbonates, dienes, esters, ethers, fluorocarbons, olefins, sytrenes, vinyl acetals, vinyl and vinylidene chlorides, vinyl esters, vinyl ethers and ketones, and vinylpyridine and vinylpyrrolidones polymers. In other cases, a shell includes a hydrophilic polymer, such as polymers including certain acrylics, amines, ethers, styrenes, vinyl acids, and vinyl alcohols. The polymer may be charged or uncharged. As noted herein, the particular components of the shell can be chosen so as to impart certain functionality to the structures.

Where a shell includes an amphiphilic material, the material can be arranged in any suitable manner with respect to the nanostructure core and/or with each other. For instance, the amphiphilic material may include a hydrophilic group that points towards the core and a hydrophobic group that extends away from the core, or, the amphiphilic material may include a hydrophobic group that points towards the core and a hydrophilic group that extends away from the core. Bilayers of each configuration can also be formed.

The structures described herein may also include one or more proteins, polypeptides and/or peptides (e.g., synthetic peptides, amphiphilic peptides). In one set of embodiments, the structures include proteins, polypeptides and/or peptides that can increase the rate of cholesterol transfer or the cholesterol-carrying capacity of the structures. The one or more proteins or peptides may be associated with the core (e.g., a surface of the core or embedded in the core), the shell (e.g., an inner and/or outer surface of the shell, and/or embedded in the shell), or both. Associations may include covalent or non-covalent interactions (e.g., hydrophobic and/or hydrophilic interactions, electrostatic interactions, van der Waals interactions).

An example of a suitable protein that may associate with a structure described herein is an apolipoprotein, such as apolipoprotein A (e.g., apo A-I, apo A-II, apo A-IV, and apo A-V), apolipoprotein B (e.g., apo B48 and apo B100), apolipoprotein C (e.g., apo C-I, apo C-II, apo C-III, and apo C-IV), and apolipoproteins D, E, and H. Specifically, apo A1, apo A2, and apo E promote transfer of cholesterol and cholesteryl esters to the liver for metabolism and may be useful to include in structures described herein. Additionally or alternatively, a structure described herein may include one or more peptide analogues of an apolipoprotein, such as one described above. A structure may include any suitable number of, e.g., at least 1, 2, 3, 4, 5, 6, or 10, apolipoproteins or analogues thereof. In certain embodiments, a structure includes 1-6 apolipoproteins, similar to a naturally occurring HDL particle. Of course, other proteins (e.g., non-apolipoproteins) can also be included in structures described herein.

Optionally, one or more enzymes may also be associated with a structure described herein. For example, lecithin-cholesterol acyltransferase is an enzyme which converts free cholesterol into cholesteryl ester (a more hydrophobic form of cholesterol). In naturally-occurring lipoproteins (e.g., HDL and LDL), cholesteryl ester is sequestered into the core of the lipoprotein, and causes the lipoprotein to change from a disk shape to a spherical shape. Thus, structures described herein may include lecithin-cholesterol acyltransferase to mimic HDL and LDL structures. Other enzymes such as cholesteryl ester transfer protein (CETP) which transfers esterified cholesterol from HDL to LDL species may also be included.

It should be understood that the components described herein, such as the lipids, phospholipids, alkyl groups, polymers, proteins, polypeptides, peptides, enzymes, bioactive agents, nucleic acids, and species for targeting described above (which may be optional), may be associated with a structure in any suitable manner and with any suitable portion of the structure, e.g., the core, the shell, or both. For example, one or more such components may be associated with a surface of a core, an interior of a core, an inner surface of a shell, an outer surface of a shell, and/or embedded in a shell.

Additionally, the components described herein, such as the lipids, phospholipids, alkyl groups, polymers, proteins, polypeptides, peptides, enzymes, bioactive agents, nucleic acids, and species for targeting described above, may be associated with a structure described herein prior to administration to a subject or biological sample and/or after administration to a subject or biological sample. For example, in some cases a structure described herein includes a core and a shell which is administered in vivo or in vitro, and the structure has a greater therapeutic effect after sequestering one or more components (e.g., an apolipoprotein) from a subject or biological sample. That is, the structure may use natural components from the subject or biological sample to increase efficacy of the structure after it has been administered.

A variety of methods can be used to fabricate the nanostructures described herein. Examples of methods are provided in International Patent Publication No. WO/2009/131704, filed Apr. 24, 2009 and entitled, "Nanostructures Suitable for Sequestering Cholesterol and Other Molecules", which is incorporated herein by reference in its entirety for all purposes.

In other embodiments, a composition is introduced to a subject or a biological sample, and the structures of the composition and/or the subject or biological sample are exposed to assay conditions that can determine a disease or condition of the subject or biological sample. At least a portion of the structures may be retrieved from the subject or biological sample and an assay may be performed with the structures retrieved. The structures may be assayed for the amount and/or type of molecules bound to the structures.

As described herein, the inventive structures may be used in "pharmaceutical compositions" or "pharmaceutically acceptable" compositions, which comprise a therapeutically effective amount of one or more of the structures described herein, formulated together with one or more pharmaceutically acceptable carriers, additives, and/or diluents. The pharmaceutical compositions described herein may be useful for treating cancer or other conditions. It should be understood that any suitable structures described herein can be used in such pharmaceutical compositions, including those described in connection with the figures. In some cases, the structures in a pharmaceutical composition have a nanostructure core comprising an inorganic material and a shell substantially surrounding and attached to the nanostructure core.

The pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those structures, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The structures described herein may be orally administered, parenterally administered, subcutaneously administered, and/or intravenously administered. In certain embodiments, a structure or pharmaceutical preparation is administered orally. In other embodiments, the structure or pharmaceutical preparation is administered intravenously. Alternative routes of administration include sublingual, intramuscular, and transdermal administrations.

Pharmaceutical compositions described herein include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

The inventive compositions suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a structure described herein as an active ingredient. An inventive structure may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered structure is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the structures described herein include pharmaceutically acceptable emulsions, microemulsions, solutions, dispersions, suspensions, syrups and elixirs. In addition to the inventive structures, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions described herein (e.g., for rectal or vaginal administration) may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the body and release the structures.

Dosage forms for the topical or transdermal administration of a structure described herein include powders, sprays, ointments, pastes, foams, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to the inventive structures, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the structures described herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a structure described herein to the body. Dissolving or dispersing the structure in the proper medium can make such dosage forms. Absorption enhancers can also be used to increase the flux of the structure across the skin. Either providing a rate controlling membrane or dispersing the structure in a polymer matrix or gel can control the rate of such flux.

Ophthalmic formulations, eye ointments, powders, solutions and the like, are also contemplated as being within the scope of this invention.

Pharmaceutical compositions described herein suitable for parenteral administration comprise one or more inventive structures in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the inventive structures may be facilitated by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Delivery systems suitable for use with structures and compositions described herein include time-release, delayed release, sustained release, or controlled release delivery systems, as described herein. Such systems may avoid repeated administrations of the structures in many cases, increasing convenience to the subject and the physician. Many types of release delivery systems are available and known to those of ordinary skill in the art. They include, for example, polymer based systems such as polylactic and/or polyglycolic acid, polyanhydrides, and polycaprolactone; nonpolymer systems that are lipid-based including sterols such as cholesterol, cholesterol esters, and fatty acids or neutral fats such as mono-, di- and triglycerides; hydrogel release systems; silastic systems; peptide based systems; wax coatings; compressed tablets using conventional binders and excipients; or partially fused implants. Specific examples include, but are not limited to, erosional systems in which the composition is contained in a form within a matrix, or diffusional systems in which an active component controls the release rate. The compositions may be as, for example, microspheres, hydrogels, polymeric reservoirs, cholesterol matrices, or polymeric systems. In some embodiments, the system may allow sustained or controlled release of the active compound to occur, for example, through control of the diffusion or erosion/degradation rate of the formulation. In addition, a pump-based hardware delivery system may be used in some embodiments. The structures and compositions described herein can also be combined (e.g., contained) with delivery devices such as syringes, pads, patches, tubes, films, MEMS-based devices, and implantable devices.

Use of a long-term release implant may be particularly suitable in some cases. "Long-term release," as used herein, means that the implant is constructed and arranged to deliver therapeutic levels of the composition for at least about 30 or about 45 days, for at least about 60 or about 90 days, or even longer in some cases. Long-term release implants are well known to those of ordinary skill in the art, and include some of the release systems described above.

Injectable depot forms can be made by forming microencapsule matrices of the structures described herein in biodegradable polymers such as polylactide-polyglycolide. Depending on the ratio of structure to polymer, and the nature of the particular polymer employed, the rate of release of the structure can be controlled. Examples of other biodegradable polymers include poly(orthoesters) and poly (anhydrides).

When the structures described herein are administered as pharmaceuticals, to humans and animals, they can be given per se or as a pharmaceutical composition containing, for example, about 0.1% to about 99.5%, about 0.5% to about 90%, or the like, of structures in combination with a pharmaceutically acceptable carrier.

The administration may be localized (e.g., to a particular region, physiological system, tissue, organ, or cell type) or systemic, depending on the condition to be treated. For example, the composition may be administered through parental injection, implantation, orally, vaginally, rectally, buccally, pulmonary, topically, nasally, transdermally, surgical administration, or any other method of administration where access to the target by the composition is achieved. Examples of parental modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be useful for some treatments because of the convenience to the patient as well as the dosing schedule.

Regardless of the route of administration selected, the structures described herein, which may be used in a suitable hydrated form, and/or the inventive pharmaceutical compositions, are formulated into pharmaceutically-acceptable dosage forms by conventional methods known to those of skill in the art.

The compositions described herein may be given in dosages, e.g., at the maximum amount while avoiding or minimizing any potentially detrimental side effects. The compositions can be administered in effective amounts, alone or in a combinations with other compounds. For example, when treating cancer, a composition may include the structures described herein and a cocktail of other compounds that can be used to treat cancer. When treating conditions associated with abnormal lipid levels, a composition may include the structures described herein and other compounds that can be used to reduce lipid levels (e.g., cholesterol lowering agents).

The phrase "therapeutically effective amount" as used herein means that amount of a material or composition comprising an inventive structure which is effective for producing some desired therapeutic effect in a subject at a reasonable benefit/risk ratio applicable to any medical treatment. Accordingly, a therapeutically effective amount may, for example, prevent, minimize, or reverse disease progression associated with a disease or bodily condition. Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

The effective amount of any one or more structures described herein may be from about 10 ng/kg of body weight to about 1000 mg/kg of body weight, and the frequency of administration may range from once a day to once a month. However, other dosage amounts and frequencies also may be used as the invention is not limited in this respect. A subject may be administered one or more structure described herein in an amount effective to treat one or more diseases or bodily conditions described herein.

An effective amount may depend on the particular condition to be treated. The effective amounts will depend, of course, on factors such as the severity of the condition being treated; individual patient parameters including age, physical condition, size and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular inventive structure employed, the route of administration, the time of administration, the rate of excretion or metabolism of the particular structure being employed, the duration of the treatment, other drugs, compounds and/or materials used in combination with the particular structure employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the structures described herein employed in the pharmaceutical composition at levels lower than that required to achieve the desired therapeutic effect and then gradually increasing the dosage until the desired effect is achieved.

In some embodiments, a structure or pharmaceutical composition described herein is provided to a subject chronically. Chronic treatments include any form of repeated administration for an extended period of time, such as repeated administrations for one or more months, between a month and a year, one or more years, or longer. In many embodiments, a chronic treatment involves administering a structure or pharmaceutical composition repeatedly over the life of the subject. For example, chronic treatments may involve regular administrations, for example one or more times a day, one or more times a week, or one or more times a month. In general, a suitable dose such as a daily dose of a structure described herein will be that amount of the structure that is the lowest dose effective to produce a therapeutic effect. Such an effective dose will generally depend upon the factors described above. Generally doses of the structures described herein for a patient, when used for the indicated effects, will range from about 0.0001 to about 100 mg per kg of body weight per day. The daily dosage may range from 0.001 to 50 mg of compound per kg of body weight, or from 0.01 to about 10 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms. For example, instructions and methods may include dosing regimens wherein specific doses of compositions, especially those including structures described herein having a particular size range, are administered at specific time intervals and specific doses to achieve reduction of cholesterol (or other lipids) and/or treatment of disease while reducing or avoiding adverse effects or unwanted effects.

While it is possible for a structure described herein to be administered alone, it may be administered as a pharmaceutical composition as described above. The present invention also provides any of the above-mentioned compositions useful for diagnosing, preventing, treating, or managing a disease or bodily condition packaged in kits, optionally including instructions for use of the composition. That is, the kit can include a description of use of the composition for participation in any disease or bodily condition, including those associated with abnormal lipid levels. The kits can further include a description of use of the compositions as discussed herein. The kit also can include instructions for use of a combination of two or more compositions described herein. Instructions also may be provided for administering the composition by any suitable technique, such as orally, intravenously, or via another known route of drug delivery.

The kits described herein may also contain one or more containers, which can contain components such as the structures, signaling entities, and/or biomolecules as described. The kits also may contain instructions for mixing, diluting, and/or administrating the compounds. The kits also can include other containers with one or more solvents, surfactants, preservatives, and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are used, the liquid form may be concentrated or ready to use. The solvent will depend on the particular inventive structure and the mode of use or administration. Suitable solvents for compositions are well known and are available in the literature.

The kit, in one set of embodiments, may comprise one or more containers such as vials, tubes, and the like, each of the containers comprising one of the separate elements to be used in the method. For example, one of the containers may comprise a positive control in the assay. Additionally, the kit may include containers for other components, for example, buffers useful in the assay.

As used herein, a "subject" or a "patient" refers to any mammal (e.g., a human), for example, a mammal that may be susceptible to a disease or bodily condition such as a disease or bodily condition associated with abnormal lipid levels. Examples of subjects or patients include a human, a non-human primate, a cow, a horse, a pig, a sheep, a goat, a dog, a cat or a rodent such as a mouse, a rat, a hamster, or a guinea pig. Generally, the invention is directed toward use with humans. A subject may be a subject diagnosed with a certain disease or bodily condition or otherwise known to have a disease or bodily condition. In some embodiments, a subject may be diagnosed as, or known to be, at risk of developing a disease or bodily condition.

In some embodiments, a subject may be diagnosed with, or otherwise known to have, a disease or bodily condition associated with cancer, as described herein. Cancers include, but are not limited to, basal cell carcinoma, biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g. small cell and non-small cell); lymphoma including Hodgkin's and Non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas.

A "biological sample," as used herein, is any cell, body tissue, or body fluid sample obtained from a subject. Non-limiting examples of body fluids include, for example, lymph, saliva, blood, urine, and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Example 1

Methods

Nanoparticle Synthesis and Formulation

HDL-Drug NPs were synthesized by first co-incubating 5 nm colloidal gold with apolipoprotein A-1 (ApoA1)—a primary constituent of endogenous human HDL (hHDL). Two lipids, 1,2-ipalmitoylsn-glycero-3-phosphoethanolamine-N-[3-(2-pyridyldithio)propionate] (PDP PE) and 1,2-dipalmitoyl-snglycero-3-phosphocholine (DPPC) were then added, along with the drug doxorubicin. Particles were concentrated and purified by tangential flow filtration (TFF) to remove impurities and un-formed starting materials.

Nanoparticle Characterization

HDL-Drug NPs were characterized in three ways. Hydrodynamic radius was measured by dynamic light scattering. Surface charge (zeta-potential) was measured. Stoichiometry of drug molecules to nanoparticles (loading efficiency) was calculated by comparing fluorescence of HDL-Doxorubicin NPs to a standard curve.

Cell Culture

Ramos, Jurkat, and SUDHL4 cells were cultured in RPMI 1640 media with 10% fetal bovine serum (FBS), 1% penicillin/streptomycin, 1% glutamax, 1% HEPES buffer. Cells were incubated at 37° C. in 5% CO2. LNCaP cells were cultured in RPMI 1640 media with 10% FBS and 1% penicillin/streptomycin. MDA MB 231 cells were cultured in DMEM/F12 media with 5% FBS, 1% sodium pyruvate, 1% PSG, and 1% penicillin/streptomycin. H9c2 cells were cultured in DMEM media with 10% FBS and 1% penicillin/streptomycin.

Cell Viability Assays

For suspension cell lines (Ramos, Jurkat, and SUDHL4), confluent cells were deposited onto 96-well plates at $1 \times 10^5$ cells/mL, then treated with either: 1-10 nM HDL NP, 1-10 nM HDL-drug NP, 10 nM-1 µM free drug, or 10 nM human HDL. All solutions were in 1% PBS, in a total volume of 100 µL. Cells were incubated for 48 hours with the treatment, then assessed for viability using a 3-(4,5-dimethylthiazol-2-yl)-5-(3-carboxymethoxyphenyl)-2-(4-sulfo-phenyl)-2H-tetrazolium (MTS) cell proliferation assay. 20 µL of the MTS solution (G1112; Promega) was added to each well; absorbance at 490 nm was measured immediately and after 90 min. Survival for a sample was presented as absorbance for that sample at 90 min, compared to absorbance for the non-treated control at 90 min. Since metabolically active cells reduce MTS, lower absorbance indicates cell death.

For adherent lines (LNCaP, MDA-MB-231, and H9c2), cells were deposited onto 96-well plates at a concentration of $5 \times 10^4$ cells/mL, 24 hours prior to treatment. Cells were then treated, incubated, and assessed as described above for the suspension cells.

Example 2

Results

Doxorubicin-Loaded Nanoparticles are Synthesized and Characterized

Figure 2:
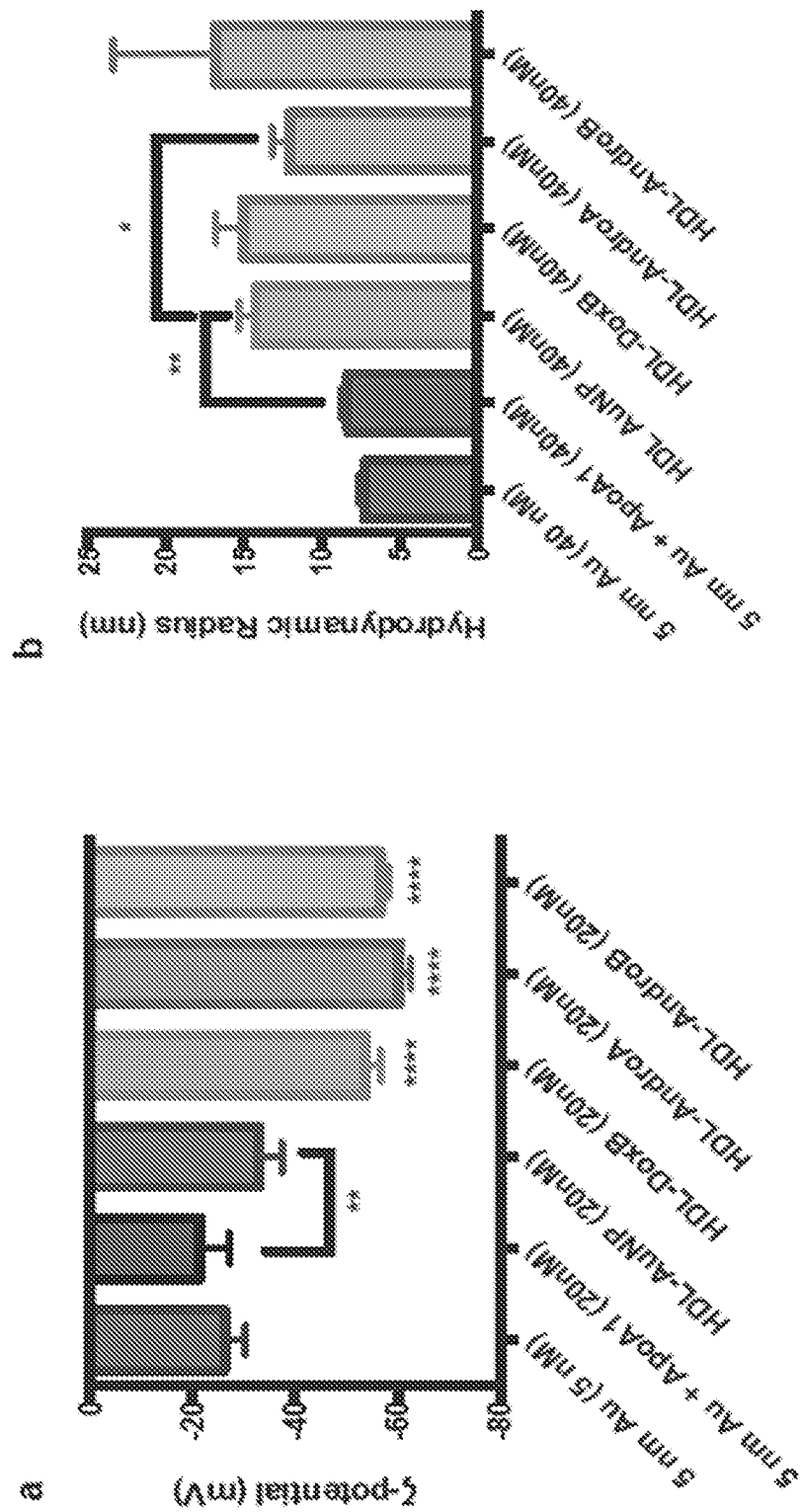
FIGS. 2A-2B show HDL-Drug NP characterization.

Particles loaded with the drug doxorubicin have been synthesized, following the scheme in FIG. 1. Characterization by dynamic light scattering (FIG. 2B) provides evidence that particles are ~15 nm—similar in size to previously demonstrated particles[5,20,23]. A shift in zeta-potential suggests surface modifications have occurred due to drug decoration.

Figure 3:
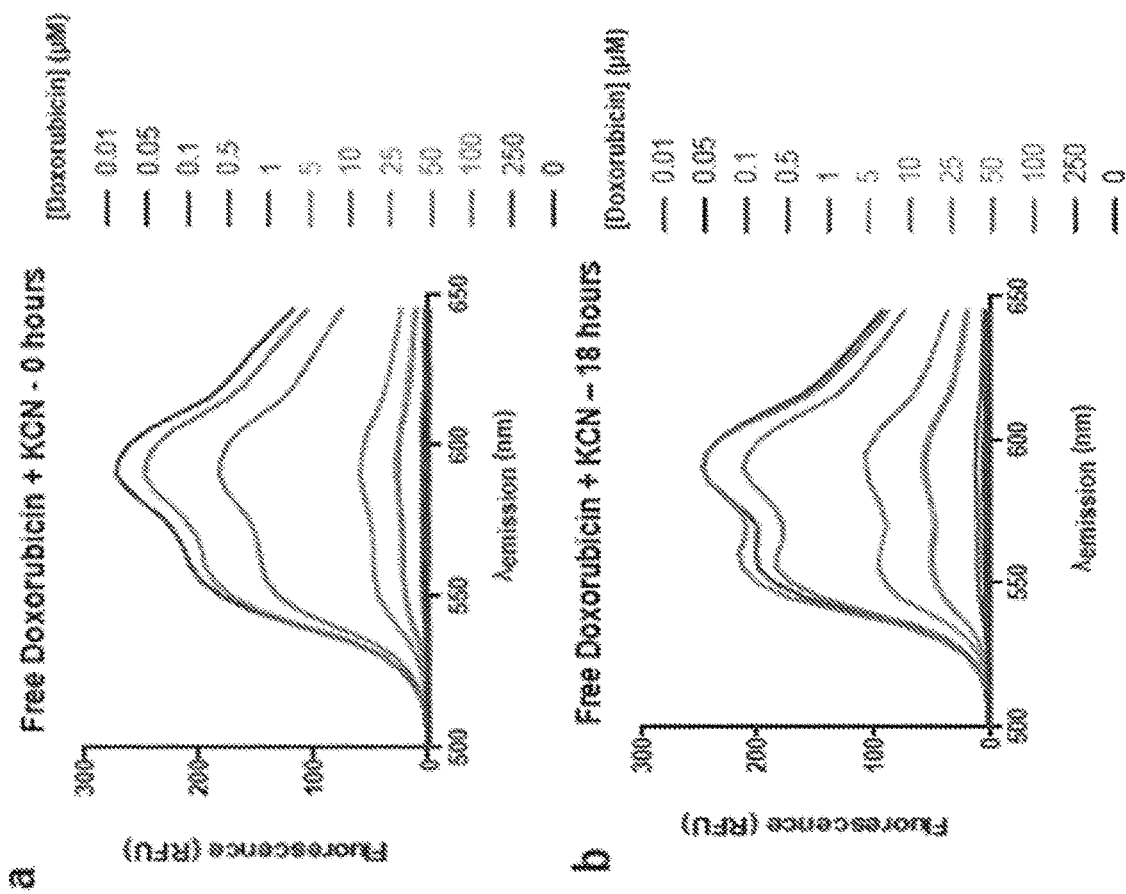
FIGS. 3A-3D show the stoichiometry quantification of HDL-Doxorubicin NPs. Fluorescence emission intensity (λ excitation=479 nm) of free doxorubicin is shown (FIG. 3A) before and (FIG. 3B) 18 hours after treatment with KCN and fluorescence emission intensity (λ excitation=479 nm) of HDL NP/Doxorubicin NPs with KCN (FIG. 3C) before and (FIG. 3D) 18 hours after treatment with KCN.
Figure 3:
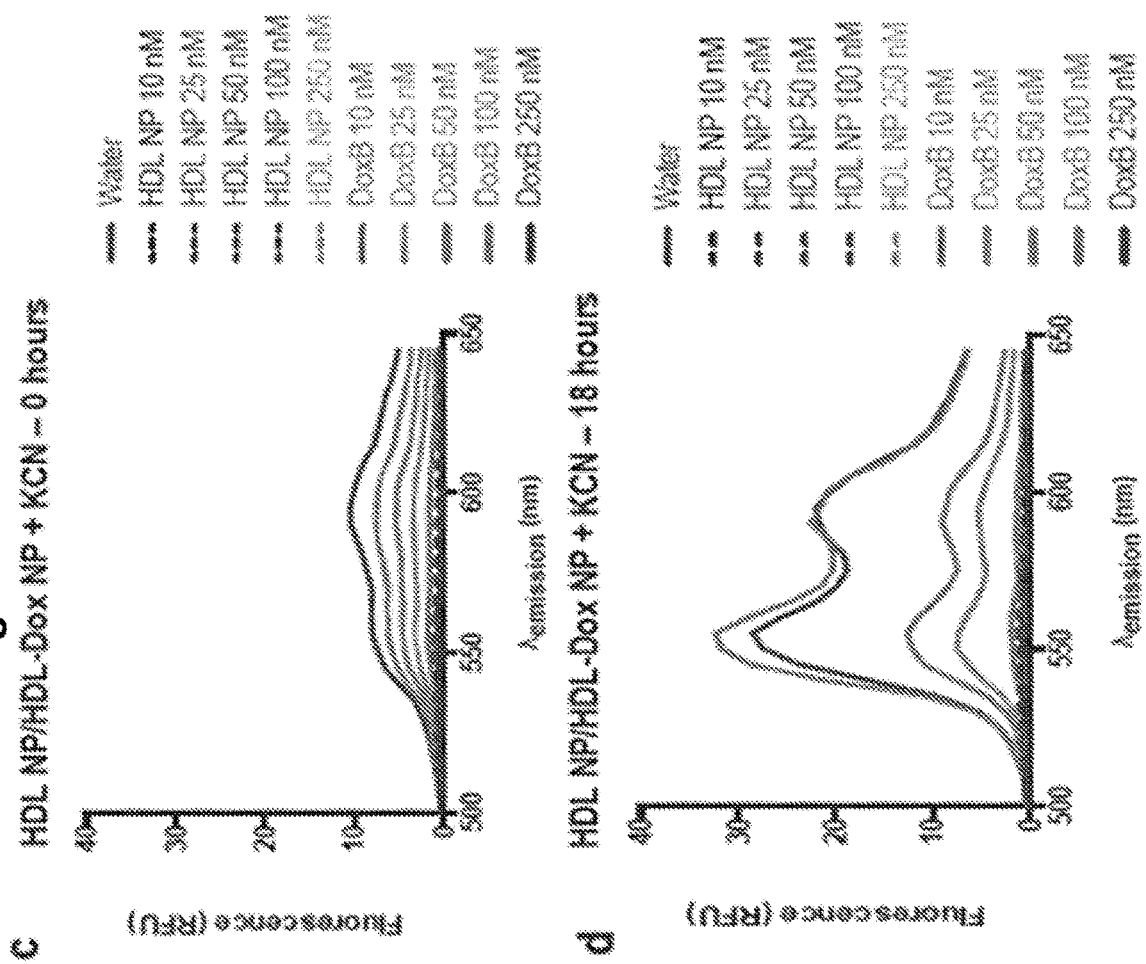
Figure 4:
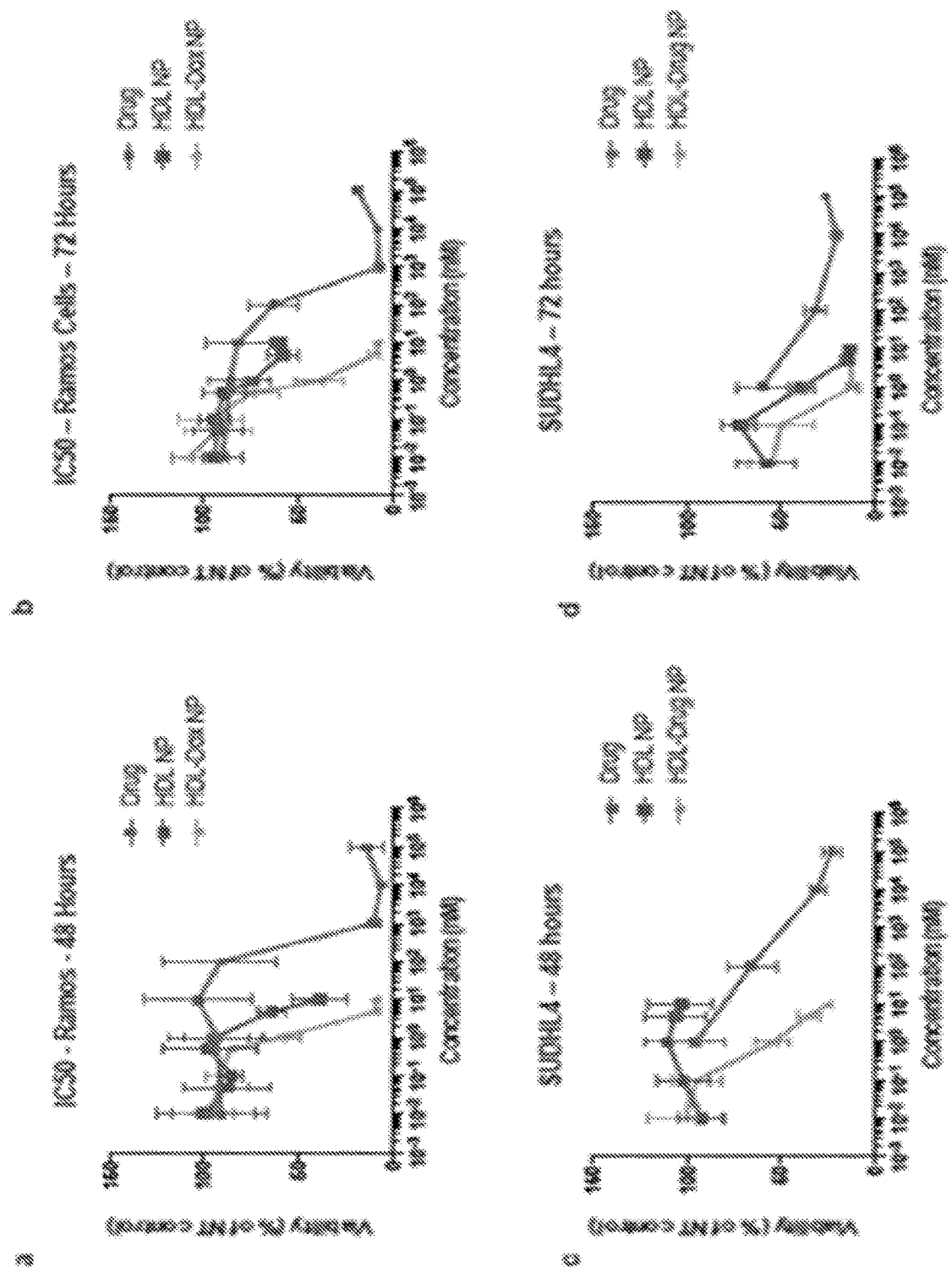
FIGS. 4A-4F show the cell viability in lymphoma cell lines after nanoparticle treatment. HDL-Doxorubicin NPs show substantial improvements in cytotoxic efficiency compared to HDL NPs in Ramos cells after (FIG. 4A) 48 and (FIG. 4B) 72 hours. Likewise, HDL-Doxorubicin NPs improves killing efficiency in SUDHL-4 cells at (FIG. 4C) 48 hours and (FIG. 4D) 72 hours.
Figure 4:
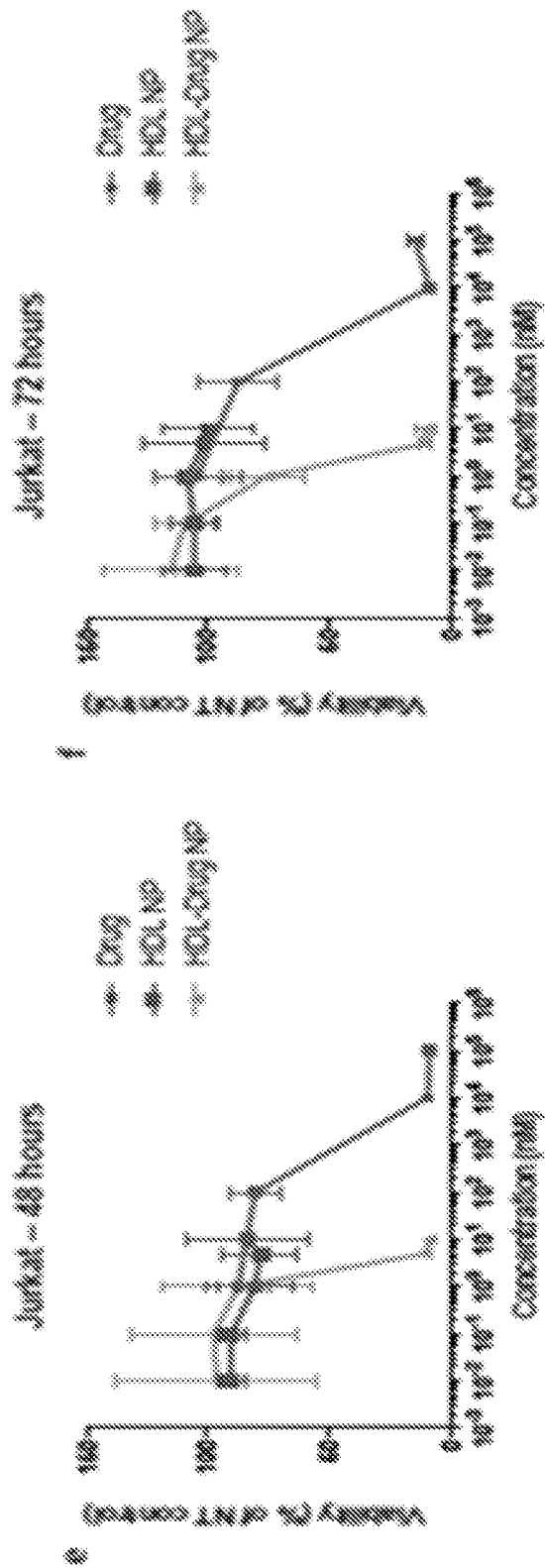
Figure 5:
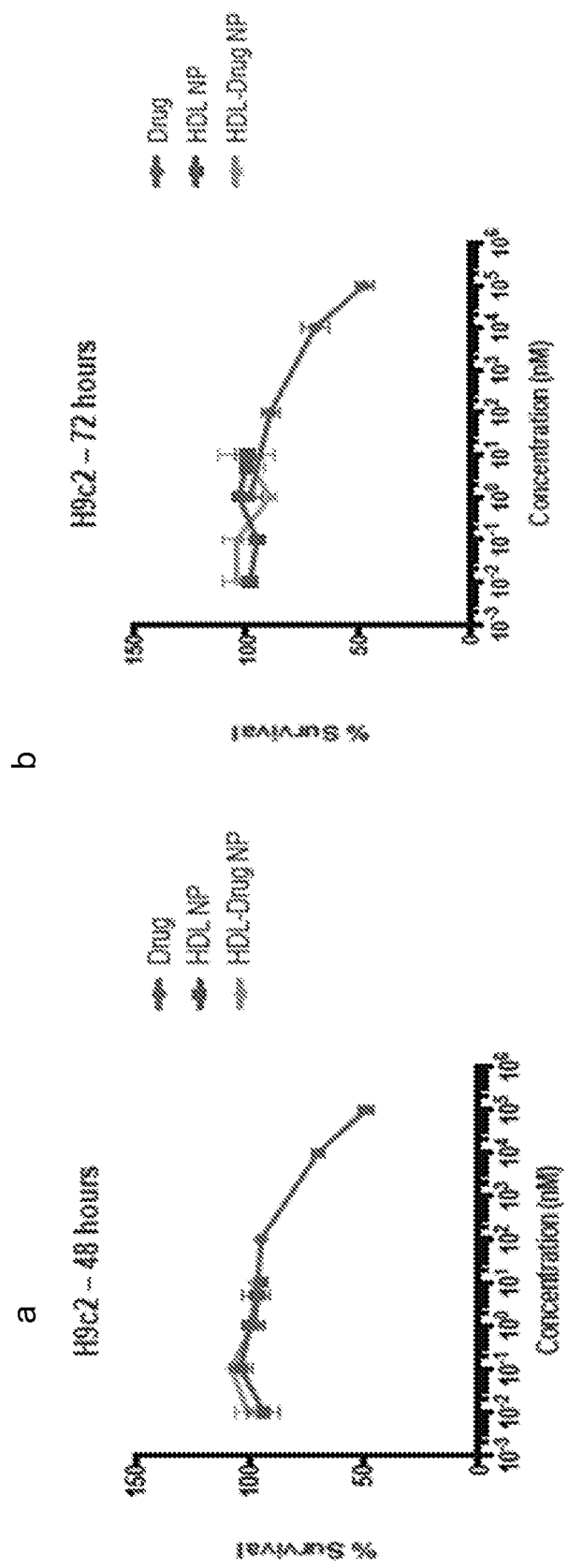
FIGS. 5A-5B show cell viability in cardiomyoblasts (H9c2) after nanostructure (NP) treatment. 48- and 72-hour treatments are shown in FIGS. 5A and 5B, respectively. No significant reduction in viability is observed after treatment with HDL-Doxorubicin NPs (HDL-Drug NP).
Figure 6:
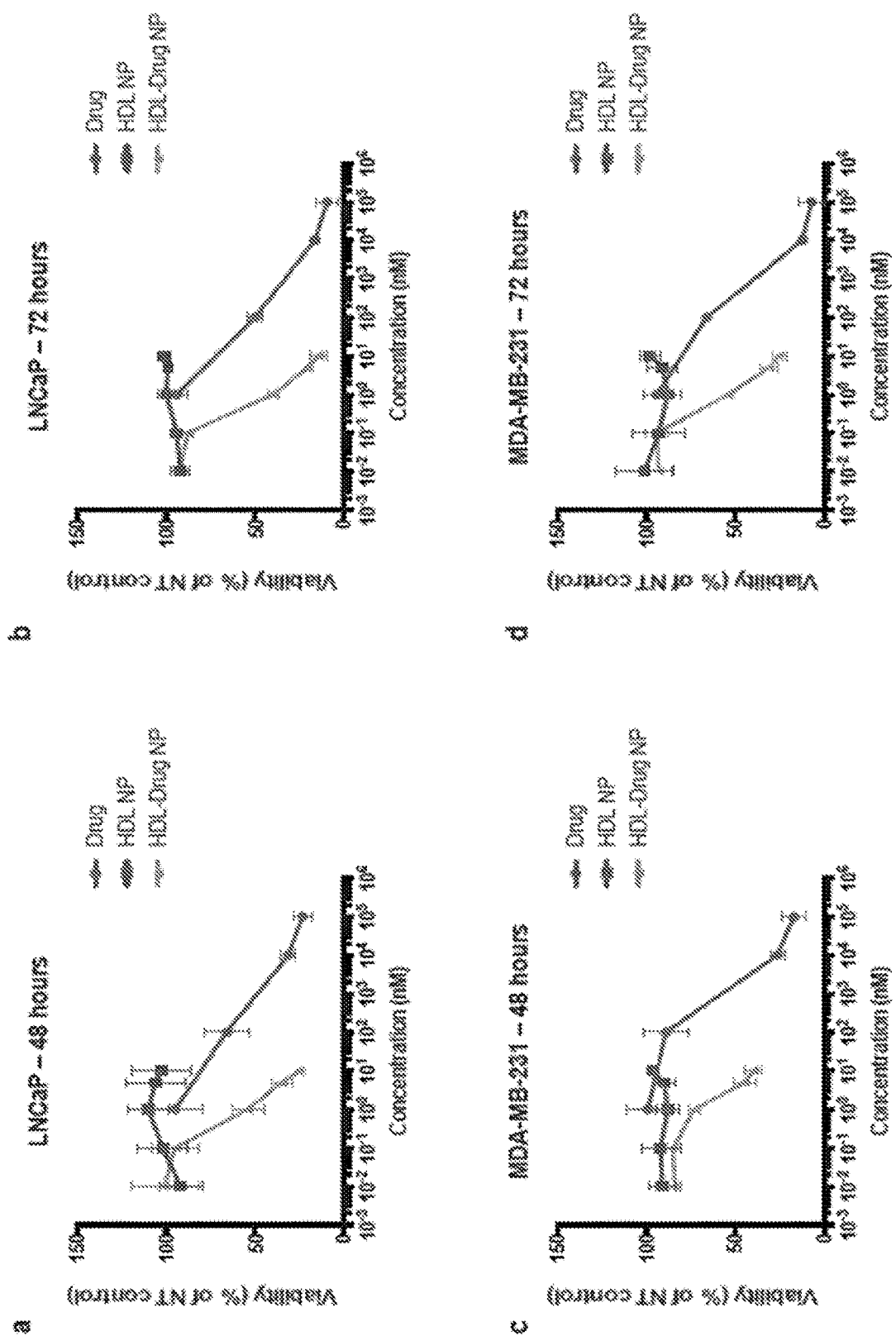
FIGS. 6A-6D show cell viability in other cancers after treatment with nanostructures (HDL NP and HDL-drug NP). LNCaP cells after 48- and 72-hour treatment are shown in FIGS. 6A and 6B, respectively. MDA MB 231 cells after 48- and 72-hour treatment are shown in FIGS. 6C and 6D, respectively.
Figure 7:
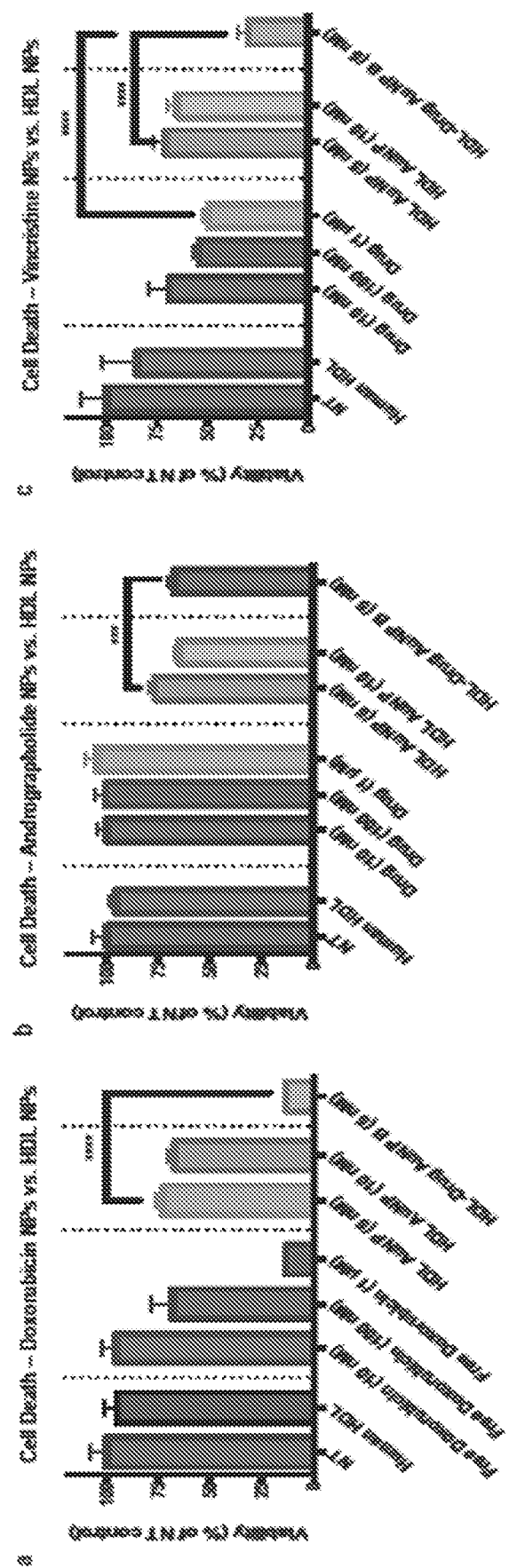
FIGS. 7A-7C show cell killing with other drugs. Doxorubicin nanoparticles (HDL-Drug AuNP) are shown in FIG. 7A. Free Doxorubicin has substantial killing effect at high concentrations (100 nM-1 μM). Killing effects comparable to those of the free drug at 1 μM are observed with HDL-Doxorubicin NP at just 5 nM, a 250-fold lower concentration. Andrographolide nanoparticles are shown in FIG. 7B. Free drug has slight protective effect on cells. HDL nanoparticle has significant killing effect, but HDL-Andrographolide NP (HDL-Drug AuNP) improves killing effect significantly at 5 nM. Vincristine nanoparticles are shown in FIG. 7C. Free drug kills with comparable efficiency to the bare HDL NP. Killing is substantially improved by formulation of the drug on the nanoparticle—compared to both the bare HDL NP and the free drug—indicating a synergistic killing effect occurs involving both the drug and the nanoparticle.

To quantify the number of doxorubicin molecules per nanoparticle, fluorescence of particles was measured before and after treatment with potassium cyanide (KCN). Doxorubicin is naturally fluorescent in solution, but its fluorescence would be quenched on the surface of a gold nanoparticle.[24,25] KCN is known to dissolve gold solids, so fluorescence recovery would be expected after treatment of HDL-Doxorubicin NPs with KCN. Significant, concentration-dependent increases in fluorescence for HDL-Doxorubicin NPs were observed when treated with KCN (FIGS. 3C-3D), but did not observe any comparable change in fluorescence for HDL NPs.

To account for the effect of oxidation by KCN on doxorubicin, a set of solutions of doxorubicin at various concentrations were prepared, and their fluorescence spectra were measured after treatment with KCN to produce a standard curve. Using this method, it was deduced that there are approximately 34±12 doxorubicin molecules per nanoparticle.

Doxorubicin-Loaded Nanoparticles Show Enhanced Killing Efficiency in Lymphoma

Cytotoxicity of the HDL-Doxorobucin NPs was assessed by incubating with lymphoma cells in culture for 48-72 hours, and measuring cell viability by a 3-(4,5-dimethylthiazol-2-yl)-5-(3-carboxymethoxyphenyl)-2-(4-sulfophenyl)-2H-tetrazolium (MTS) assay. HDL-Drug NPs were used to treat several lymphoma cell lines. Viability of cells treated with HDL-Drug NPs was compared to that of non-treated cells, cells treated with HDL-NPs, and cells treated with the free drug in solution.

Ramos (Burkitt's Lymphoma) and Southwestern University Diffuse Histiocytic Lymphoma 4 (SUDHL-4, diffuse large B-cell lymphoma) lines were selected due to high SR-B1 expression. The Jurkat line, a T cell-derived lymphoma, was evaluated due to its lack of SR-B1 expression.[5] In Ramos, SUDHL-4, and Jurkat cells, substantially increased cytotoxic efficiency is observed for the HDL-Doxorubicin NPs compared to either the bare HDL NPs or the dissolved doxorubicin. The Doxorubicin-loaded nanoparticles show substantial killing effect at much lower concentrations than the free drug in solution. The Doxorubicin-loaded nanoparticles show significantly higher killing efficiency than HDL NPs at comparable concentrations.

Doxorubicin-Loaded Nanoparticles Show Reduced Toxicity to Cardiomyoblasts

To test whether HDL-Drug NPs could show reduce toxicity in cardiac tissue compared to free doxorubicin, HDL-Doxorubicin NPs was incubated with H9c2 cells—a rat cardiomyoblast cell line—and measured viability with an MTS assay. H9c2 cells were treated with the same concentrations of HDL-Doxorubicin NPs, HDL NPs, and free doxorubicin as the lymphoma lines above. H9c2 cells showed a significant reduction in viability at higher concentrations of doxorubicin (though less than the lymphoma cells). However, H9c2 cells showed no significant reduction in viability when treated with the HDL-Doxorubicin NPs for 72 hours.

Doxorubicin NPs Show Cytotoxicity for Various Cancers

To determine whether HDL-Drug NPs could be effective in other non-hematological malignancies two additional cell lines were treated with the particles: the LNCaP (human prostate adenocarcinoma) and MDA-MB-231 (human breast adenocarcinoma). No significant reduction in viability of these cell lines after treatment with HDL NPs was observed, but cell viability was reduced substantially when treated with the HDL Doxorubicin NPs.

Improved Killing Efficiency is Observed for Vincristine and Andrographolide-Loaded NPs in Lymphoma In addition to the HDL-Doxorubicin NPs, comparable NPs were formulated, using an identical synthetic procedure, with the drugs Andrographolide and Vincristine. Andrographolide is a diterpenoid lactone derived from the herb Andrographis paniculata, and known to have pro-apoptotic effects in lymphoma cells[26]. Vincristine is a vinca alkaloid known to have myelosuppressive effects.[27]

The HDL-Andrographolide and HDL-Vincristine NPs were not extensively characterized, but were used to treat Ramos cells. Significantly enhanced cytotoxic efficiency is observed by MTS assay for these nanoparticles; in the case of the HDL-Vincristine particles, the conjugated particles have greater absolute cytotoxicity than any tested concentration of the free drug. The strength of these results testifies to the wide applicability of this delivery system.

This study has presented a novel, targeted drug delivery system applicable to a wide range of cancers and therapeutic agents. Drug-loaded nanoparticles mimicking endogenous HDL have been formulated and characterized. In in vitro assays, these nanoparticles have demonstrated substantial increases in cytotoxic efficiency compared to drugs in solution. This suggests these nanoparticles may be a vehicle for future dose reduction for drugs (such as doxorubicin) limited in administration by toxicity. Further, the results suggest that the particles may act as targeting agents. Specifically, the study has shown that although HDL-Doxorubicin NPs very efficiently kill lymphoma cells, they have relatively low cytotoxicity for cardiac myoblasts. This suggests that the HDL-Drug NPs may be a promising vehicle for delivery of drugs with organ system toxicity (e.g. doxorubicin, which is cardiotoxic).

These results have also demonstrated the versatility of this approach. In addition to lymphoma, the HDL-Doxorubicin NPs have been shown to have cytotoxic effects in prostate and breast cancer cells. Likewise, in addition to Doxorubicin, HDL-Drug NPs are formulated with Andrographolide and Vincristine—two drugs with substantially different structures and mechanisms. The HDL-Andrographolide and HDL-Vincristine NPs are shown, like HDL-Doxorubicin, to have enhanced cytotoxic efficiency. This demonstrates that other lipophilic or amphipathic drugs could be formulated using this system. The system could therefore increase the applicability of existing cytotoxic compounds that are difficult to formulate due to poor aqueous solubility, or conversely improve the cytotoxicity of easily-formulated compounds with only mild effect in solution (e.g. andrographolide).

REFERENCES

1. Cho, K., Wang, X., Nie, S., Chen, Z. G. & Shin, D. M. et al. Therapeutic nanoparticles for drug delivery in cancer. *Clin. Cancer Res.* 14, 1310-1316 (2008).

2. Akhter, S., Ahmad, M. Z., Ahmad, F. J., Storm, G. & Kok, R. J. et al. Gold nanoparticles in theranostic oncology: current state-of-the-art. *Expert Opin Drug Deliv* 9, 1225-1243 (2012).
3. Asztalos, B. F., Tani, M. & Schaefer, E. J. et al. Metabolic and functional relevance of HDL subspecies. *Current Opinion in Lipidology* 22, 176-185 (2011).
4. Barter, P. et al. HDL cholesterol, very low levels of LDL cholesterol, and cardiovascular events. *N. Engl. J. Med.* 357, 1301-1310 (2007).
5. Yang, S. et al. Biomimetic, synthetic HDL nanostructures for lymphoma. *Proceedings of the National Academy of Sciences* 110, 2511-2516 (2013).
6. Ghosh, M. et al. Curcumin nanodisks: formulation and characterization. *Nanomedicine: Nanotechnology, Biology and Medicine* 7, 162-167 (2011).
7. Singh, A. T. K., Ghosh, M., Forte, T. M., Ryan, R. O. & Gordon, L. I. et al. Curcumin nanodisk-induced apoptosis in mantle cell lymphoma. *Leuk. Lymphoma* 52, 1537-1543 (2011).
8. Singh, A. T. K. et al. All trans retinoic acid nanodisks enhance retinoic acid receptor mediated apoptosis and cell cycle arrest in mantle cell lymphoma. *Br. J. Haematol.* 150, 158-169 (2010).
9. Outomuro, D., Grana, D. R., Azzato, F. & Milei, J. et al. Adriamycin-induced myocardial toxicity: New solutions for an old problem? *International Journal of Cardiology* 117, 6-15 (2007).
10. Singal, P., Li, T., Kumar, D., Danelisen, I. & Iliskovic, N. et al. Adriamycin-induced heart failure: mechanisms and modulation. *Molecular and Cellular Biochemistry* 207, 77-86 (2000).
11. Singal, P. K., Iliskovic, N., Li, T. & Kumar, D. et al. Adriamycin cardiomyopathy: pathophysiology and prevention. (1997). at <www.fasebj.org/content/11/12/931.short>
12. Gaitanis, A. & Staal, S. et al. in (Grobmyer, S. R. & Moudgil, B. M.) 385-392 (Humana Press, 2010). at <www.springerlink.com/index/10.1007/978-1-60761-609-2_26.
13. Chen, W. et al. Redox and pH-responsive degradable micelles for dually activated intracellular anticancer drug release. *J Control Release* 169, 171-179 (2013).
14. Sun, Y. et al. Bioreducible PAA-g-PEG graft micelles with high doxorubicin loading for targeted antitumor effect against mouse breast carcinoma. *Biomaterials* 34, 6818-6828 (2013).
15. Hekmatara, T. et al. Efficient systemic therapy of rat glioblastoma by nanoparticle-bound doxorubicin is due to antiangiogenic effects. *Clinical neuropathology* 28, 153-164 (2009).
16. Bibby, D. C. et al. Pharmacokinetics and biodistribution of RGD-targeted doxorubicin-loaded nanoparticles in tumor-bearing mice. *Int J Pharm* 293, 281-290 (2005).
17. Cao, Y. et al. Self-assembled nanoparticle drug delivery systems from galactosylated polysaccharide-doxorubicin conjugate loaded doxorubicin. *International Journal of Biological Macromolecules* 46, 245-249 (2010).
18. Ding, J. et al. Efficacious hepatoma-targeted nanomedicine self-assembled from galactopeptide and doxorubicin driven by two-stage physical interactions. *J Control Release* 169, 193-203 (2013).
19. Wang, F. et al. Doxorubicin-tethered responsive gold nanoparticles facilitate intracellular drug delivery for overcoming multidrug resistance in cancer cells. *ACS Nano* 5, 3679-3692 (2011).
20. Thaxton, C. S., Daniel, W. L., Giljohann, D. A., Thomas, A. D. & Mirkin, C. A. et al. Templated Spherical High Density Lipoprotein Nanoparticles. *J. Am. Chem. Soc.* 131, 1384-1385 (2009).
21. Bonadonna, G., Zucali, R., Monfardini, S., De Lena, M. & Uslenghi, C. et al. Combination chemotherapy of Hodgkin's disease with adriamycin, bleomycin, vinblastine, and imidazole carboxamide versus MOPP. *Cancer* 36, 252-259 (1975).
22. Fisher, R. I. et al. Comparison of a standard regimen (CHOP) with three intensive chemotherapy regimens for advanced non-Hodgkin's lymphoma. *N. Engl. J. Med.* 328, 1002-1006 (1993).
23. Luthi, A. J. et al. Tailoring of Biomimetic High-Density Lipoprotein Nanostructures Changes Cholesterol Binding and Efflux. *ACS Nano* 6, 276-285 (2012).
24. Karukstis, K. K., Thompson, E. H., Whiles, J. A. & Rosenfeld, R. J. et al. Deciphering the fluorescence signature of daunomycin and doxorubicin. *Biophys. Chem.* 73, 249-263 (1998).
25. Fan, C. et al. Beyond superquenching: hyper-efficient energy transfer from conjugated polymers to gold nanoparticles. *Proceedings of the National Academy of Sciences of the United States of America* 100, 6297-6301 (2003).
26. Yang, S. et al. Mitochondrial-mediated apoptosis in lymphoma cells by the diterpenoid lactone andrographolide, the active component of *Andrographis paniculata*. *Clin. Cancer Res.* 16, 4755-4768 (2010).
27. Johnson, I. S., Armstrong, J. G., Gordan, M. & Burnett, J. P. et al. The Vinca Alkaloids: a New Class of Oncolytic Agents. *Cancer Res.* 23, 1390-1427 (1963).

Example 3

Methods

Nanoparticle Synthesis and Formulation

HDL-Drug NPs were synthesized by first co-incubating 5 nm colloidal gold (Ted Pella) with a fivefold molar excess of ApoA1 (Meridian Life Sciences) at room temperature for 1 hour while shaking gently. After diluting the mixture by 20% with pure ethanol, two lipids and (where applicable) the anti-cancer drug were added in the following order: 1. (1,2-dipalmitoyl-sn-glycero-3-phosphoethanolamine-N-[3-(2-pyridyldithio)propionate] (PDP PE) (250 molar excess over gold), 2. doxorubicin (Sigma, 100 molar excess over gold) and 1,2-dipalmitoyl-sn-glycero-3-phosphocholine (DPPC) (250 molar excess over gold). After an incubation for at least two hours at room temperature while shaking gently, particles were concentrated and purified by tangential flow filtration (TFF) to remove impurities and un-formed starting materials. Nanoparticles were stored in ddH2O at 4° C. protected from light and used within 2-3 weeks from synthesis.

Nanoparticle Characterization

HDL-NP/Dox-HDL-NP concentrations were determined by measuring absorbance at 525 nm (extinction coefficient $\epsilon 525$ nm $9.696 \times 10^6$ M-1 cm-1). Due to the small absorption coefficient of doxorubicin at 525 nm compared to gold, the presence of doxorubicin on the HDL-NP did not interfere with the determination of particle concentration.

The hydrodynamic diameter and the surface charge ($\zeta$-potential) of the Dox-HDL-NP/HDL-NPs were determined using a Malvern Zetasizer ZS.

Because of the close apposition of doxorubicin to the gold nanoparticle HDL-NP, quench doxorubicin fluorescence resulted (?) upon binding. Stoichiometry of drug molecules to bound nanoparticles was therefore calculated by releasing the drug from the Dox-HDL-NP by acid treatment, and comparing the restored fluorescence of the drug to a standard curve. While acid treatment (200 mM HCl) greatly weakens the binding affinity between the HDL NP and doxorubicin, it does not completely abolish it. To compensate for any quenching of fluorescence by un-dissociated Dox-HDL-NP, 25-75 nM HDL-NP without drug were included in the serial dilutions of doxorubicin (prepared in 200 mM HCl) for the standard curve. This standard curve was then used to assess how much doxorubicin was released from 25-75 nM Dox-HDL-NP (some amount as was used in the standard curve) upon HCl treatment.

Cell Culture

Ramos and SUDHL4 cells were cultured in RPMI 1640 media with 9% fetal bovine serum (FBS), 1% penicillin/streptomycin, 1% Glutamax®, 1% HEPES buffer. Cells were incubated at 37° C. in 5% CO2. LNCaP cells were cultured in RPMI 1640 media with 10% FBS and 1% penicillin/streptomycin. MDA MB 231 cells were cultured in DMEM/F12 media with 5% FBS, 1% sodium pyruvate, 1% PSG, and 1% penicillin/streptomycin. H9c2 cells were cultured in DMEM media with 10% FBS and 1% penicillin/streptomycin.

Cell Viability Assays

For suspension cell lines (Ramos and SUDHL4), 90 µl confluent cells were deposited into 96-well plates at 1×105 cells/mL, then treated with 10 µl of either: 1-10 nM HDL NP, 1-10 nM HDL-drug NP, 10 nM-1 µM free drug, 10 nM human HDL, or PBS. All nanoparticle/drug/HDL solutions were in 1% PBS. Cells were incubated for 48 hours with the treatment, and then assessed for viability using a 3-(4,5-dimethylthiazol-2-yl)-5-(3-carboxymethoxyphenyl)-2-(4-sulfo-phenyl)-2H-tetrazolium (MTS) cell proliferation assay. Twenty µL of the MTS solution (G1112; Promega) was added to each well; absorbance at 490 nm was measured immediately and after 90 minutes. Cells incubated with PBS were used as a 100% survival control; medium incubated with PBS was used as a 0% survival control/blank. Cell viability was calculated according to the following formula:

Cell viability=(OD$_{490, 90\ min}$(sample)−OD$_{490, 90\ min}$(0% survival control))/(OD$_{490, 90\ min}$(100% survival control)−OD$_{490, 90\ min}$(0% survival control))×100%

Since metabolically active cells reduce MTS, lower absorbance indicates cell death.

For adherent lines (LNCaP, MDA-MB-231, and H9c2), cells were deposited onto 96-well plates at a concentration of 5×104 cells/mL, 24 hours prior to treatment. Cells were then treated, incubated, and assessed as described above for the suspension cells.

Western Blot

After cell treatments, cells were washed with PBS and centrifuged. Cell pellets were lysed with Cell Extraction Buffer (Invitrogen) supplemented with Protease Inhibitor Mixture (Sigma), and the protein concentration was measured with a colorimetric BCA Protein Assay Kit (Pierce). Total protein samples (25-50 µg) were separated on 4-20% precast polyacrylamide gels (BioRad) and transferred to PVDF membranes. Membranes were blocked with 5% non-fat milk in Tris Buffered Saline-Tween (TBS-T) and incubated with primary antibodies followed by HRP-conjugated secondary antibodies. Immunoreactive proteins were visualized using enhanced chemiluminescence. Primary antibodies: rabbit anti-scavenger receptor type B-1 (anti-SR-B1; ab52629; Abcam), and anti-tubulin (2144; Cell Signaling).

Example 4

Results and Discussion

Synthesis and Characterization of HDL-NPs and Doxorubicin-Loaded HDL-NPs (Dox-HDL-NP)

The synthesis of HDL-NPs has been previously published[1, 9], and is further described in the Methods section. Briefly, HDL-NPs were synthesized by incubating 5 nm gold colloid with Apolipoprotein A1 protein (ApoA1)—a primary constituent of endogenous human HDL (hHDL)—followed by incubation with two phospholipids, 1,2-dipalmitoyl-sn-glycero-3-phosphoethanolamine-N-[3-(2-pyridyldithio)propionate (PDP-PE) and 1,2-dipalmitoyl-sn-glycero-3-phosphocholine (DPPC) in 20% ethanol (v/v). Doxorubicin-loaded HDL-NPs were synthesized in parallel using a similar strategy and with a 100-fold molar excess of doxorubicin in comparison to the gold nanoparticle template. Tangential flow filtration was used to exchange the constructs into water and to remove unreacted protein, lipids, and drug prior to further analysis.

Figure 8:
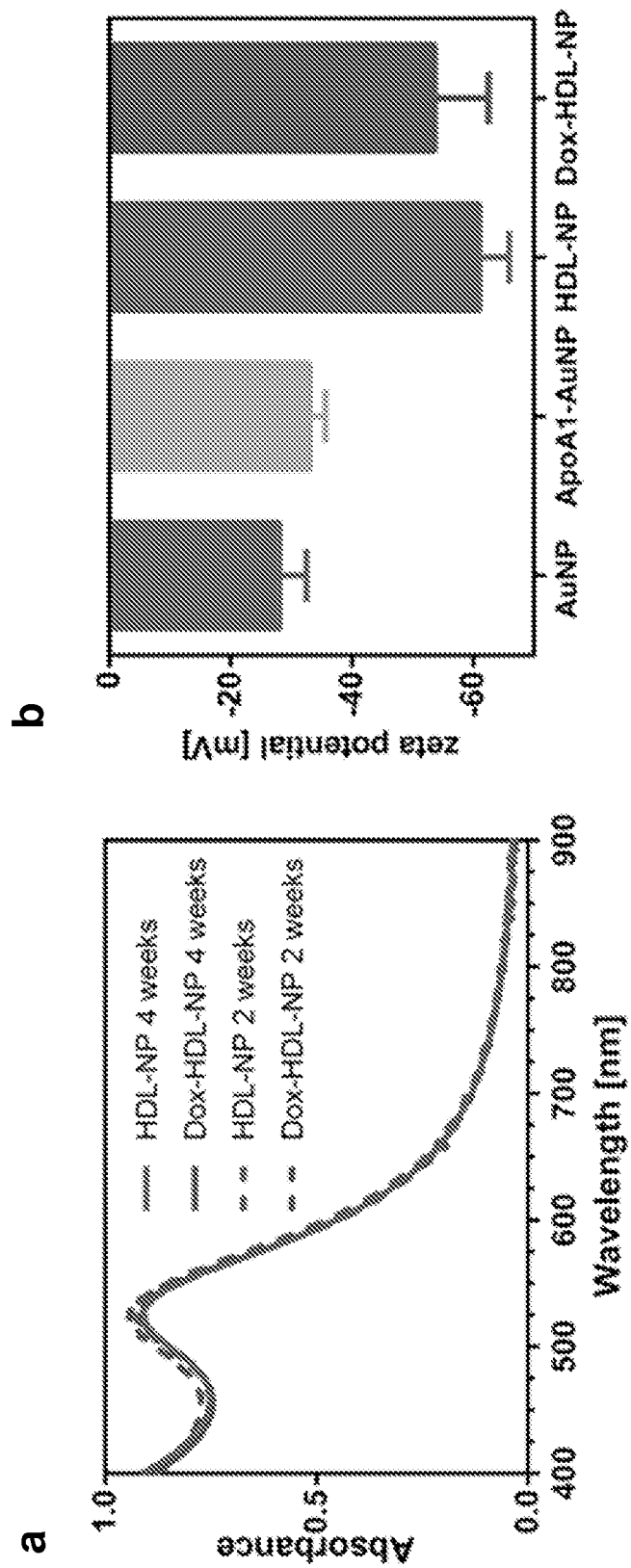
FIGS. 8A-8F show HDL-Drug NP characterization.
Figure 8:
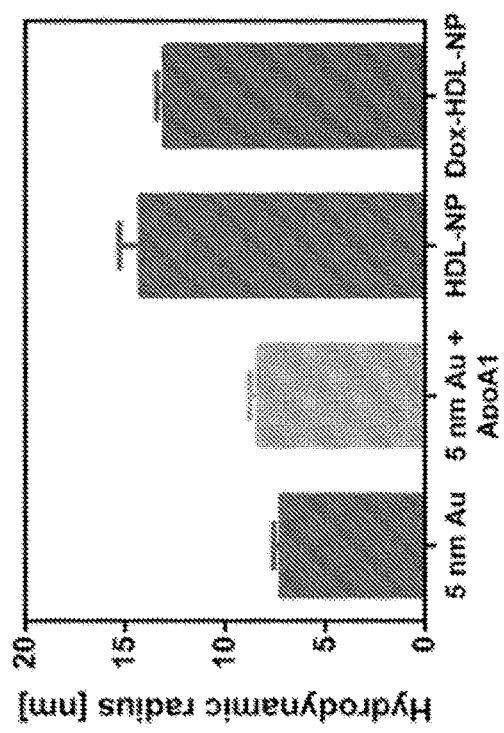
Figure 8:
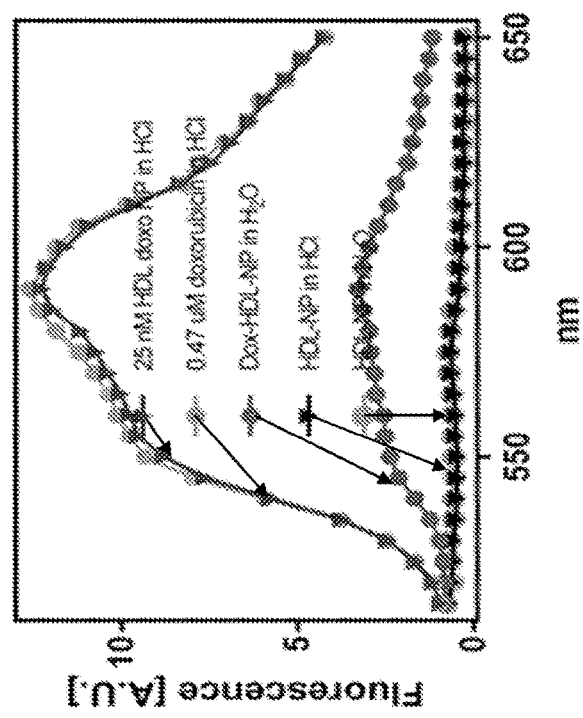
Figure 8:
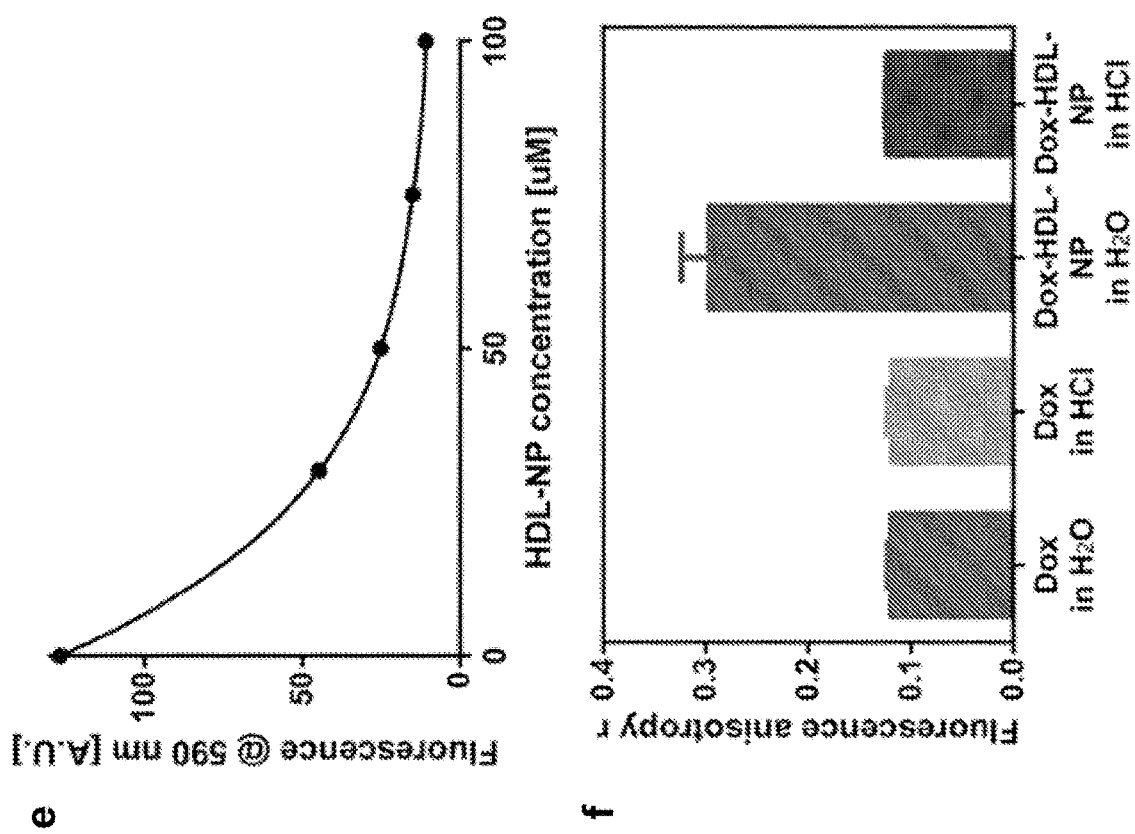

HDL-NPs and doxorubicin-loaded HDL-NPs (Dox-HDL-NPs) were first characterized in terms of stability and size by using UV-Vis spectroscopy, zeta-potential, and dynamic light scattering measurements. Disperse solutions of 5 nm gold colloid exhibit a characteristic surface plasmon band (SPB) at approximately 520 nm, while aggregated solutions red-shift.[10] Both the HDL-NPs and Dox-HDL-NPs demonstrated SPB maxima at 525 nm even after storage at 4° C. for up to 4 weeks (FIG. 8A), suggesting that the particles are stable and not prone to aggregation. Conjugate stability was further confirmed by determining the zeta-potential of the different constructs. Zeta-potential is a measure for the electrostatic repulsion or attraction of nanoparticles in solution, and its magnitude is an indication of the stability of the particle. While gold nanoparticle alone (AuNP) and gold nanoparticles conjugated to ApoA1 protein (AuNP-ApoA1) exhibit an intermediate stability (zeta potential values in the range of −30 mV), HDL-NP and Dox-HDL-NP showed a zeta-potential of significantly increased magnitude, suggesting increased stability of the complexes (FIG. 8B). Also the addition of ApoA1 and phospholipids significantly increased the hydrodynamic diameter of the gold particle as monitored by dynamic light scattering (FIG. 8C). The further addition of doxorubicin in the HDL-NP synthesis had minimal influence on the final size of the conjugate, due to the small size of doxorubicin compared to the HDL-NP and the fact that the doxorubicin is in close proximity to the gold nanoparticle surface (vide infra) (FIG. 8C).

To confirm that doxorubicin was conjugated with the NP in the Dox-HDL-NP constructs and not merely present in solution, two additional parameters were measured: doxorubicin fluorescence quenching, an indication of close proximity of the drug to the gold template,[11] and doxorubicin fluorescence anisotropy, a measure of the tumbling rate of the drug molecules in the bound versus the free state. Doxorubicin exhibits a drug-specific emission maximum of approximately 590 nm (excitation 490 nm) (FIG. 8D). However, doxorubicin fluorescence is gradually quenched when increasing concentrations of exogenous HDL-NP are added to the drug (FIG. 8lE). This is in agreement with a close apposition of the drug to the gold core[11] that would occur during binding of the drug to the NP. Consistently purified Dox-HDL-NP exhibit only a very weak, yet doxorubicin-specific, emission spectrum at neutral pH (FIG. 8D). Incubation of the Dox-HDL-NP in 0.2 M HCl rapidly decomposes the nanostructure, releases doxorubicin from the conjugate and restores drug fluorescence (FIG. 8D). Doxorubicin is known to bind to lipids mainly through electrostatic interactions, but also through hydrophobic interactions and has been shown to be able to penetrate lipid membranes.[1] The positively charged drug may bind to HDL-NP at neutral pH by interacting with the negatively charged phosphate group of the outer leaflet lipid DPPC and then intercalate into the lipid layer on the surface of the HDL-NP (FIG. 1). This interaction would be disrupted at low pH by protonation and neutralization of the phosphate group, explaining the acid-induced release of the drug from the Dox-HDL-NP. However, this binding mechanism is speculative, and binding through penetration of the drug into the lipid layers of the HDL-NP cannot currently be excluded.

As an alternative approach to confirm drug binding to the HDL-NP, conducted fluorescence anisotropy measurements exploiting the residual fluorescence of Dox-HDL-NP particles were conducted. In solution, both under neutral and acidic conditions, free doxorubicin (MW=580 Da) tumbles rapidly. Upon binding to the significantly larger HDL-NP (estimated MW of 1,800 kDa) at neutral pH, the tumbling rate of doxorubicin is significantly reduced, which is reflected by the significant increase in anisotropy (FIG. 8F). Addition of 0.2 M HCl releases doxorubicin from the conjugate and allows the drug to tumble freely in solution again. The result is a drop in fluorescence anisotropy to the values observed for free doxorubicin (FIG. 8F).

Figure 9:
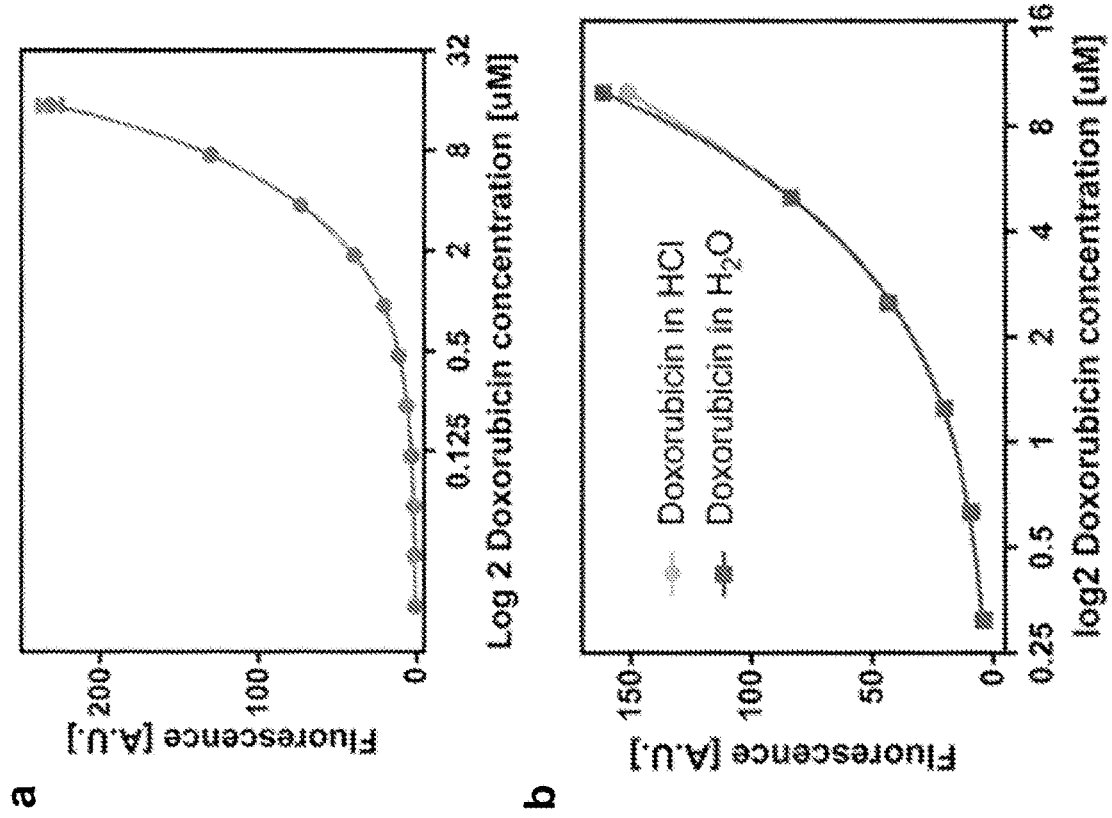
FIG. 9A-9B depict doxorubicin standard curves under different conditions.
Figure 10:
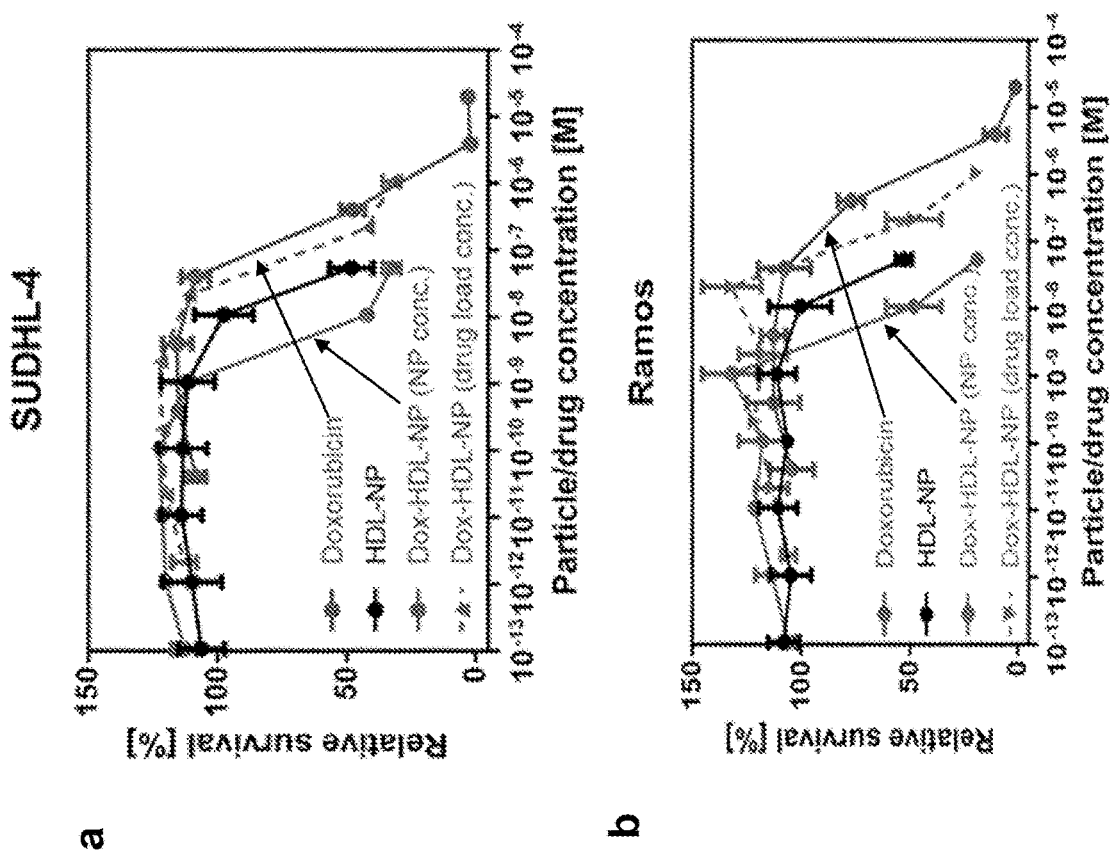
FIG. 10A-10B illustrates cell viability in lymphoma cell lines after nanoparticle treatment. Dox-HDL-NP show substantial improvements in cytotoxic efficiency compared to HDL-NPs and free doxorubicin in Ramos (FIG. 10A) and SUDHL4 (FIG. 10B) cells after 48 hours. Survival was adjusted to cells treated with PBS instead of drug/NP (100% survival) and to medium treated with PBS (0% survival).
Figure 11:
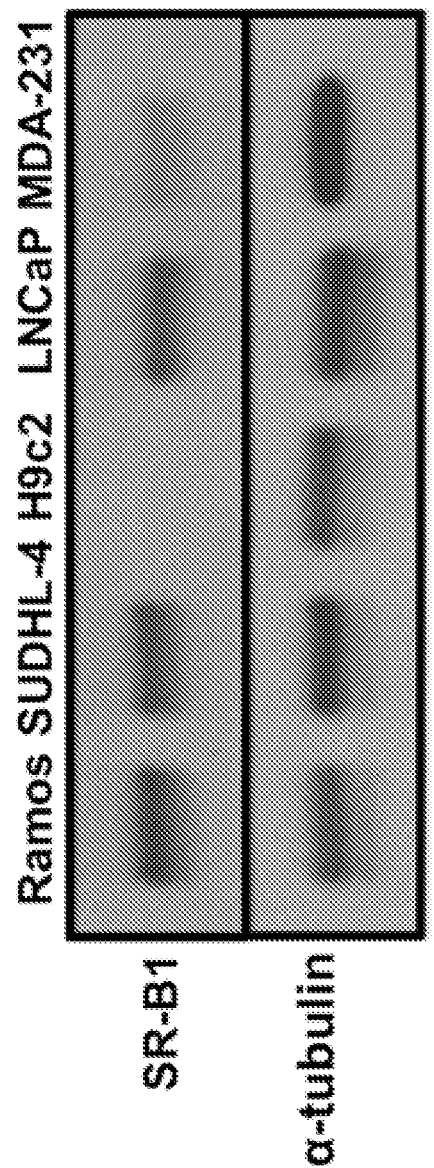
FIG. 11 demonstrates the expression of the HDL receptor SR-B1 in cultured cancer cell lines as determined by Western blotting. Tubulin was used as a loading control.
Figure 12:
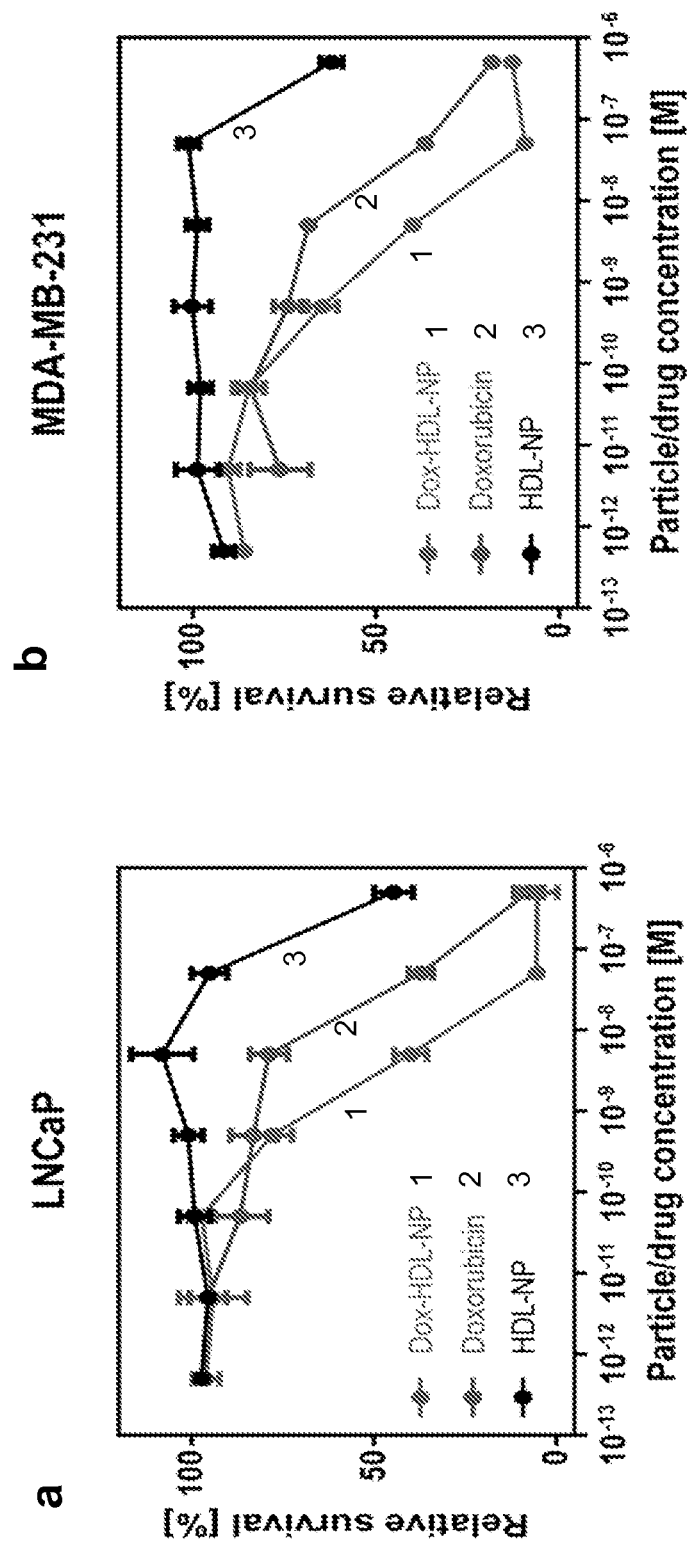
FIG. 12A-12B shows cell viability in breast and prostate cancer cell lines after nanoparticle treatment. Dox-HDL-NP show substantial improvements in cytotoxic efficiency compared to HDL-NPs and free doxorubicin in LNCaP (human prostate adenocarcinoma) (FIG. 12A) and MDA-MB-231 (human breast adenocarcinoma) (FIG. 12B) cells after 48 hours. Survival was adjusted to cells treated with PBS instead of drug/NP (100% survival) and to medium treated with PBS (0% survival).
Figure 13:
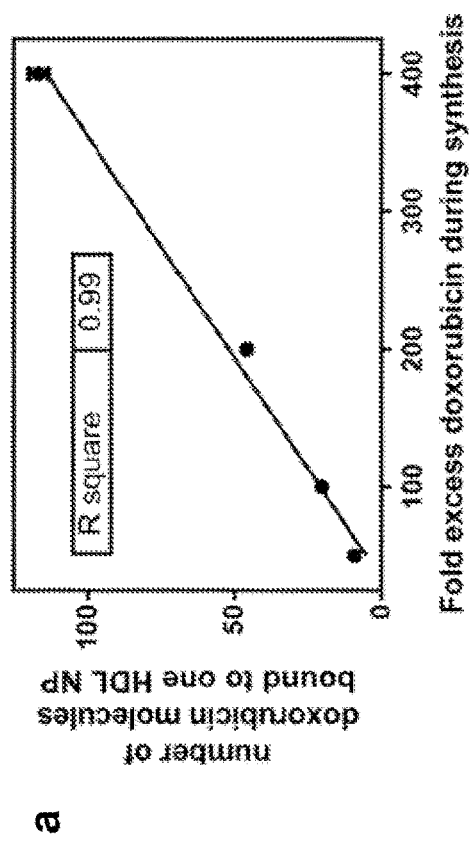
FIG. 13A-13C shows cell viability in lymphoma cell lines after nanoparticle treatment.
Figure 13:
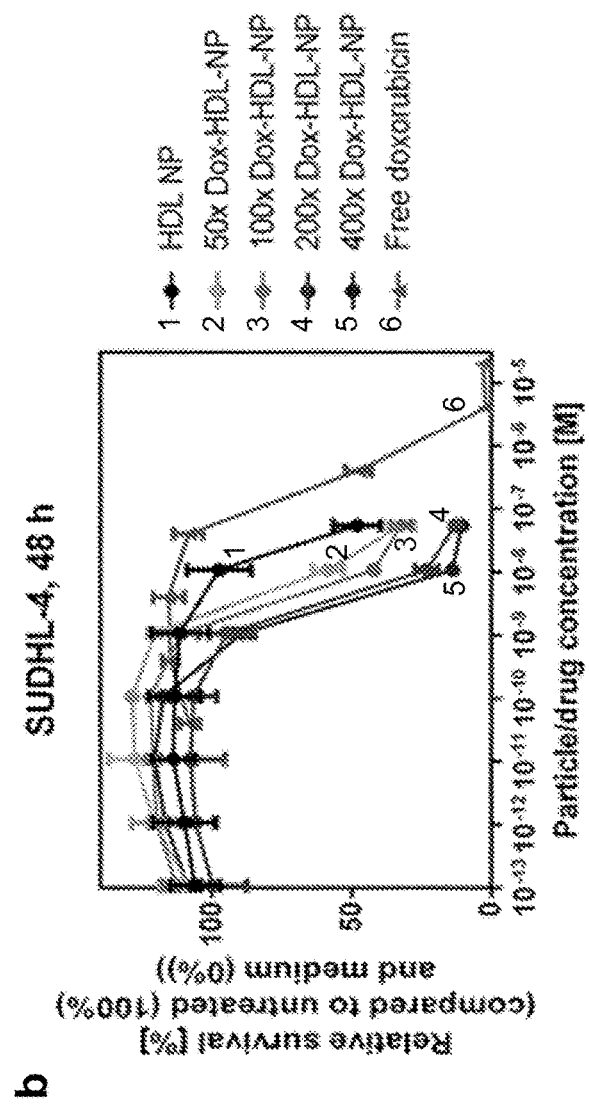
Figure 13:
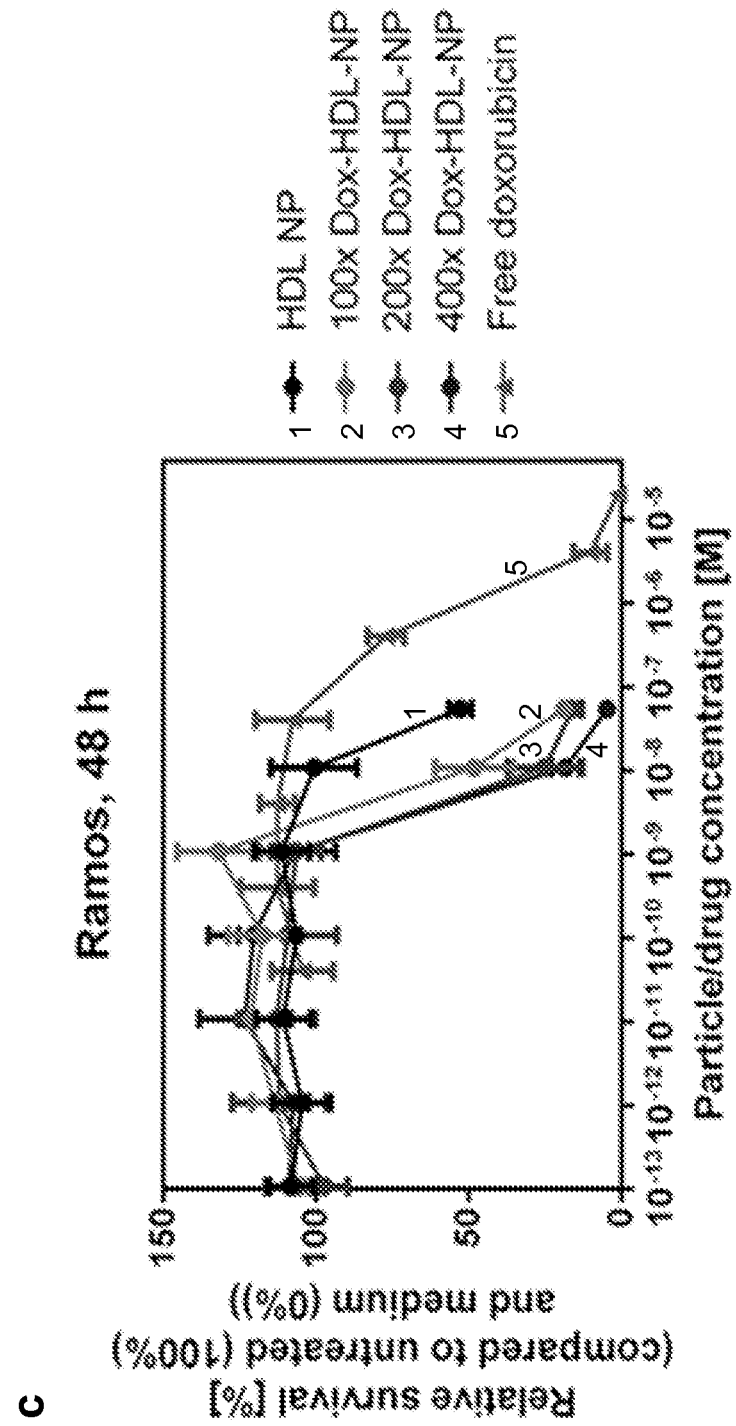
Figure 14:
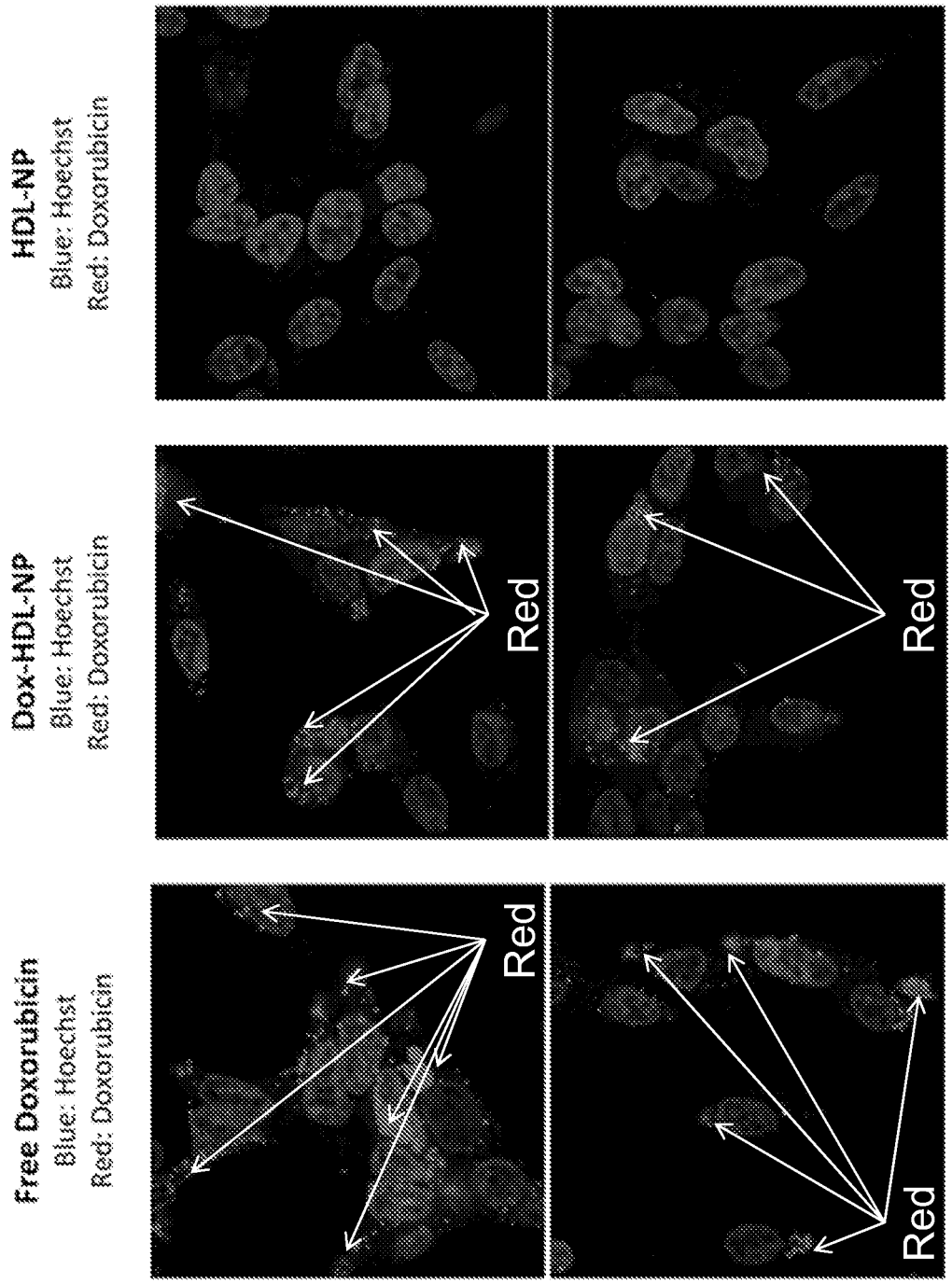
FIG. 14 shows images of prostate cancer cells treated with free doxorubicin, Dox-HDL-NP, and HDL-NP, DAPI fluorescence is shown in blue, doxorubicin fluorescence is shown in red.

To further characterize the Dox-HDL-NP conjugate, stoichiometric studies were undertaken, taking advantage of the endogenous fluorescence of doxorubicin (FIG. 8D). As expected, HDL-NP conjugates without drug are not fluorescent, while Dox-HDL-NPs exhibit a drug-characteristic, but largely quenched, fluorescence emission spectrum (FIG. 8D). Doxorubicin was released from the Dox-HDL-NP by addition of HCl, which restored doxorubicin fluorescence. By comparing the fluorescence intensity of the doxorubicin released from a known amount of Dox-HDL-NP to a doxorubicin standard curve (FIG. 9A), it was determined that approximately 20 doxorubicin molecules are bound per nanoparticle. Importantly, the increase in doxorubicin fluorescence is not simply the result of a change in pH, since doxorubicin fluorescence in water and in 0.2 M HCl is virtually identical (FIG. 9B).

Doxorubicin-Loaded HDL-NP Show Enhanced Cytotoxicity in Lymphoma

Cytotoxicity of the Dox-HDL-NPs was assessed by incubating Dox-HDL-NP, HDL-NP, or free doxorubicin at varying doses with different lymphoma cell lines. Ramos (a Burkitt's Lymphoma cell line) and Southwestern University Diffuse Histiocytic Lymphoma (SUDHL-4) cell lines were selected because of their high surface expression of SR-B1, the surface receptor previous studies have shown mediate uptake of HDL-NP.[1] Conjugates were incubated with cells for 48 hours and cell viability was assessed using the 3-(4,5-dimethylthiazol-2-yl)-5-(3-carboxymethoxyphenyl)-2-(4-sulfophenyl)-2H-tetrazolium (MTS) assay. MTS is a colorimetric assay which monitors the reduction of MTS to a formazan product with an absorbance maximum of 490 nm, and increases in proportion to the number of reducing equivalents produced by cells present in the assay. Even without drug-conjugation, bare HDL-NPs are effective in killing the lymphoma cell lines Ramos and SUDHL4 and are also more effective in killing lymphoma cell lines than free doxorubicin. Importantly, Dox-HDL-NPs exhibit increased cytotoxicity when compared to either HDL-NP alone or free doxorubicin in both cell lines, suggesting a combined cytotoxic effect from both the HDL-NP nanocarrier as well as the delivered doxorubicin. Consistent with the observation that HDL-NP and Dox-HDL-NP exhibit cytotoxicity in Ramos and SUDHL4 cells, both cell lines express significant amounts of SR-B1 receptor, a receptor which is known to interact with endogenous HDL and mediate cholesterol uptake from this natural nanocarrier (11).

Doxorubicin-Loaded HDL-NP Show Enhanced Cytotoxicity in Breast and Prostate Cancer Cell Lines To test if drug-loaded HDL-NP are capable of effectively killing lymphoma cancer cell lines and have efficacy in the treatment of other types of cancer, the use of HDL-NPs in two additional cell lines which express the SR-B1 receptor was examined: LNCaP (human prostate adenocarcinoma) and MDA-MB-231 (human breast adenocarcinoma) cell lines (11). Prostate and breast cancers are the most commonly diagnosed cancers and are the second most common causes of cancer death in American men and women, respectively. HDL-NP in both cell lines exhibit modest cytotoxic effects which are greatly enhanced by loading with doxorubicin (12), suggesting that Dox-HDL-NP may be promising treatment options for breast and prostate cancer as well.

Increasing Doxorubicin Loading on HDL-NPs Enhances Killing Effect in Lymphoma Cells Next, a suite of doxorubicin-HDL-NP with varying doxorubicin to HDL-NP stoichiometries was synthesized. Fold excess of doxorubicin to HDL-NP in the syntheses ranged from 50-fold to 400-fold. To assess the number of doxorubicin molecules per HDL-NP in the purified conjugates, doxorubicin fluorescence was measured and compared to a standard curve after disrupting the synthesized conjugates with 0.2 M HCl. This analysis demonstrated that loaded doxorubicin per HDL-NP increases linearly across the range of synthesis stoichiometries measured (13). In both SUDHL-4 and Ramos cell lines, doxorubicin-HDL-NP designs with increased doxorubicin incorporation lead to increased killing.

Fluorescence Microscopy of Doxorubicin Uptake in Prostate Cancer Cell Lines

To further confirm delivery of doxorubicin to cancer cells with HDL-NP, LNCaP adenocarcinoma cell lines were assessed by fluorescence microscopy after treatment with free doxorubicin, Dox-HDL-NP, and HDL-NP. At 18 hours after treatment, fluorescence was clearly seen in the free doxorubicin-treated cells, while minimal autofluorescence was seen in the HDL-NP treated cells (14). Furthermore, subcellular distribution of doxorubicin fluorescence was similar in the free doxorubicin and Dox-HDL-NP conditions, suggesting that delivery of doxorubicin on HDL-NP avoids endosomal sequestration.

Limited Cytotoxicity of Dox-HDL-NP in Cardiomyoblasts

The sse of doxorubicin is limited clinically by cardiotoxicity, which manifests most typically as heart failure resulting from reduced cardiac function. The targeted cells are the contractile cells of the heart called cardiomyocytes. This toxicity typically occurs when the cumulative dose of doxorubicin administered exceeds 450 mg/m$^2$ of body surface area. Numerous studies have demonstrated the efficacy of doxorubicin in several solid tumor malignancies. However, dose-limiting side effects circumscribe its use and in some instances prevent its use in patients in whom doxorubicin may be clinically effective. The effects of Dox-HDL-NP and free doxorubicin in H9c2 cardiomyoblasts, a rat-derived cardiomyocyte cell line that has been used extensively in mechanistic studies of doxorubicin toxicity in heart cells, have been studied. At therapeutic concentrations (the respective concentration where the particle or the drug leads to complete killing of the Ramos lymphoma cell line), Dox-HDL NPs are significantly less cytotoxic toward cardiomyocytes than free doxorubicin (15).

Figure 15:
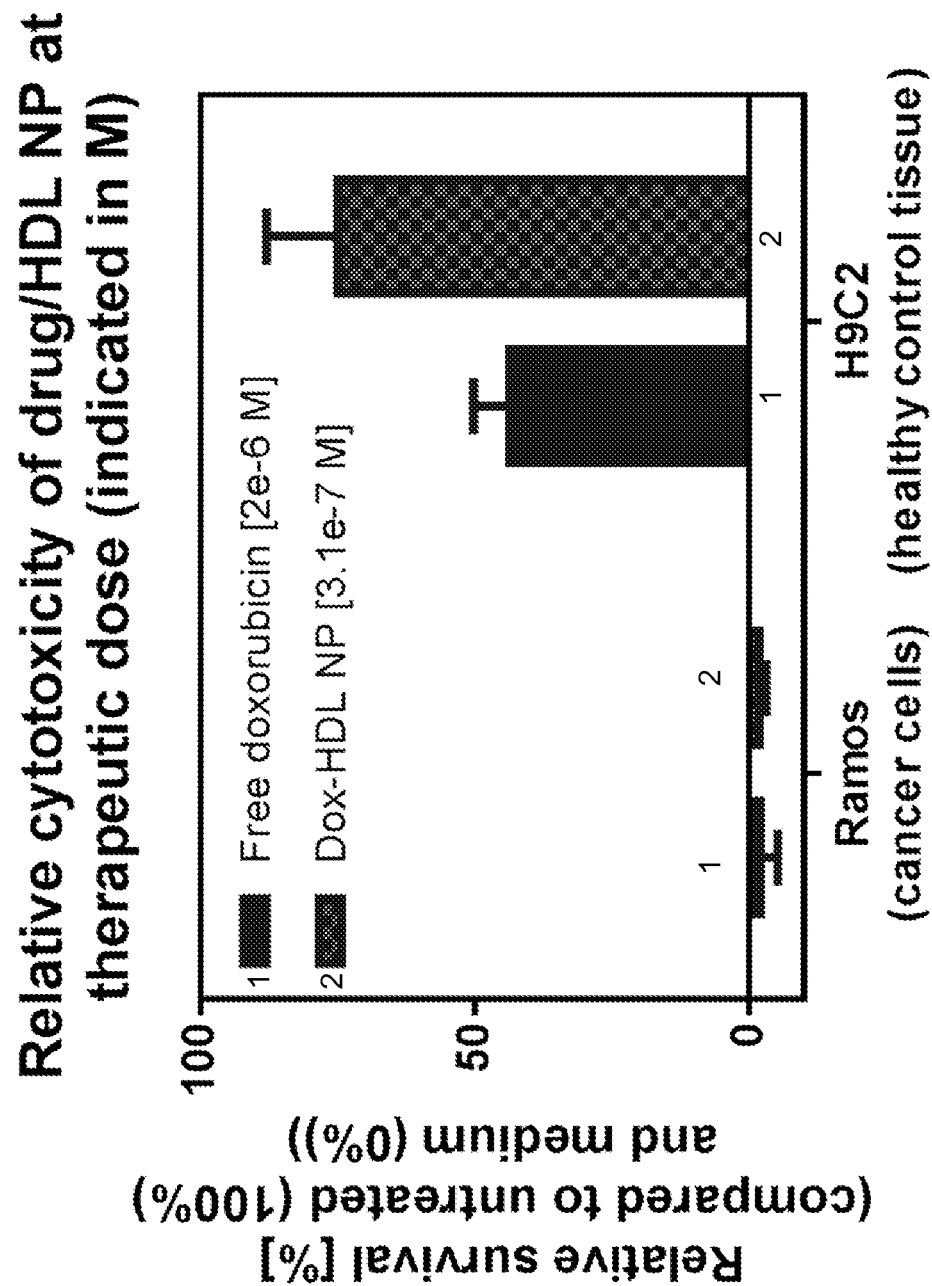
FIG. 15 shows the relative cytotoxicity of Dox-HDL NP and free doxorubicin at therapeutic dose (dose at which the respective constructs kills Ramos cells). H9C2 is a healthy rat-derived cardiomyocyte cell line.

Consistent with the decreased cytotoxicity of Dox-HDL-NP in H9c2 cells, SR-B1 expression in H9c2 cells was not detected (11). As a control for the fact that H9c2 cells are of rat origin, while the other cell lines studied were of human origin, Western blot of rat-derived HepG2 cells (a liver cancer cell line) was also performed, which demonstrated that the antibody used also detects rat SR-B1 (FIG. 15).

Vincristine-Loaded HDL-NP Show Enhanced Cytotoxicity in Lymphoma

Figure 16:
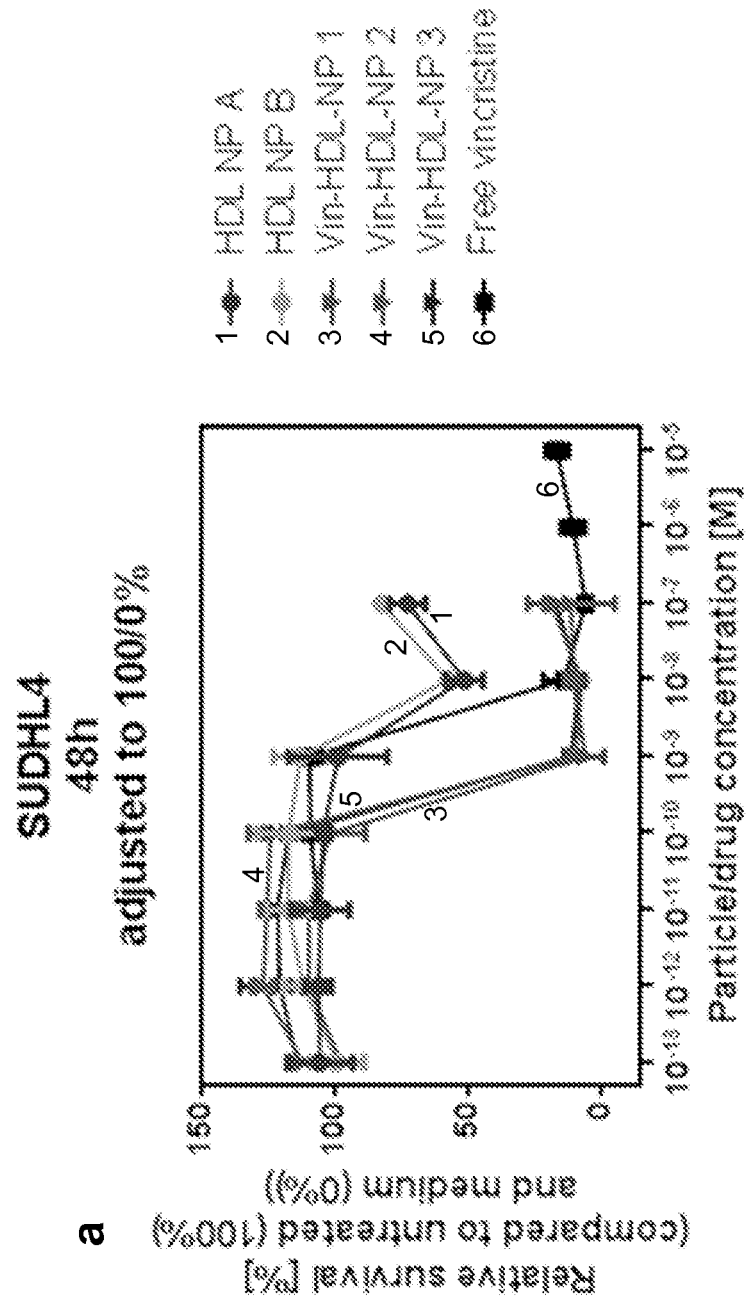
FIG. 16A-16B shows the cell viability of different conjugates from the MTS assay. Conjugates were incubated with Ramos (FIG. 16B) and SUDHL-4 lymphoma (FIG. 16A) cell lines for 48 hours and cell viability was assessed using the MTS assay.
Figure 16:
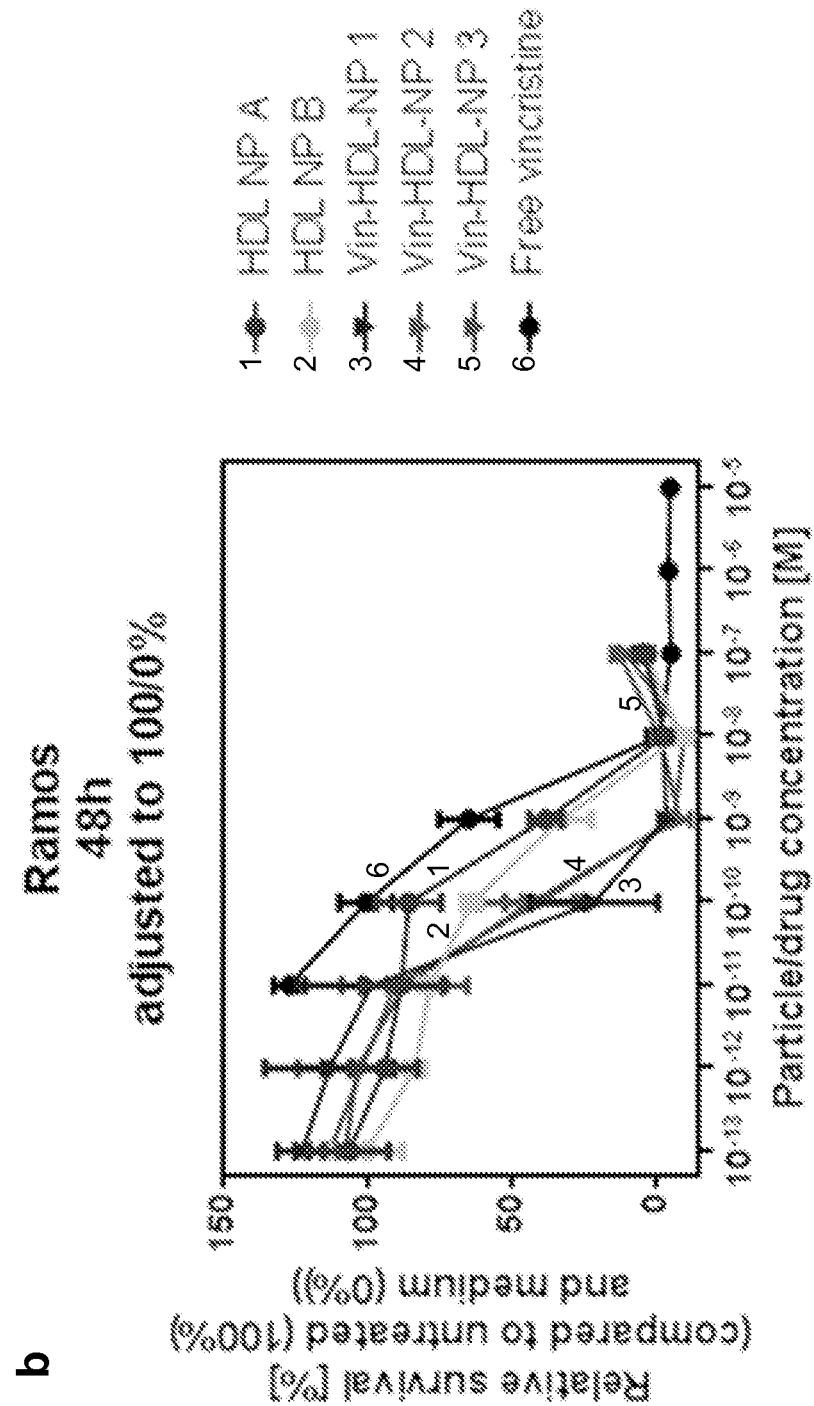
Figure 17:
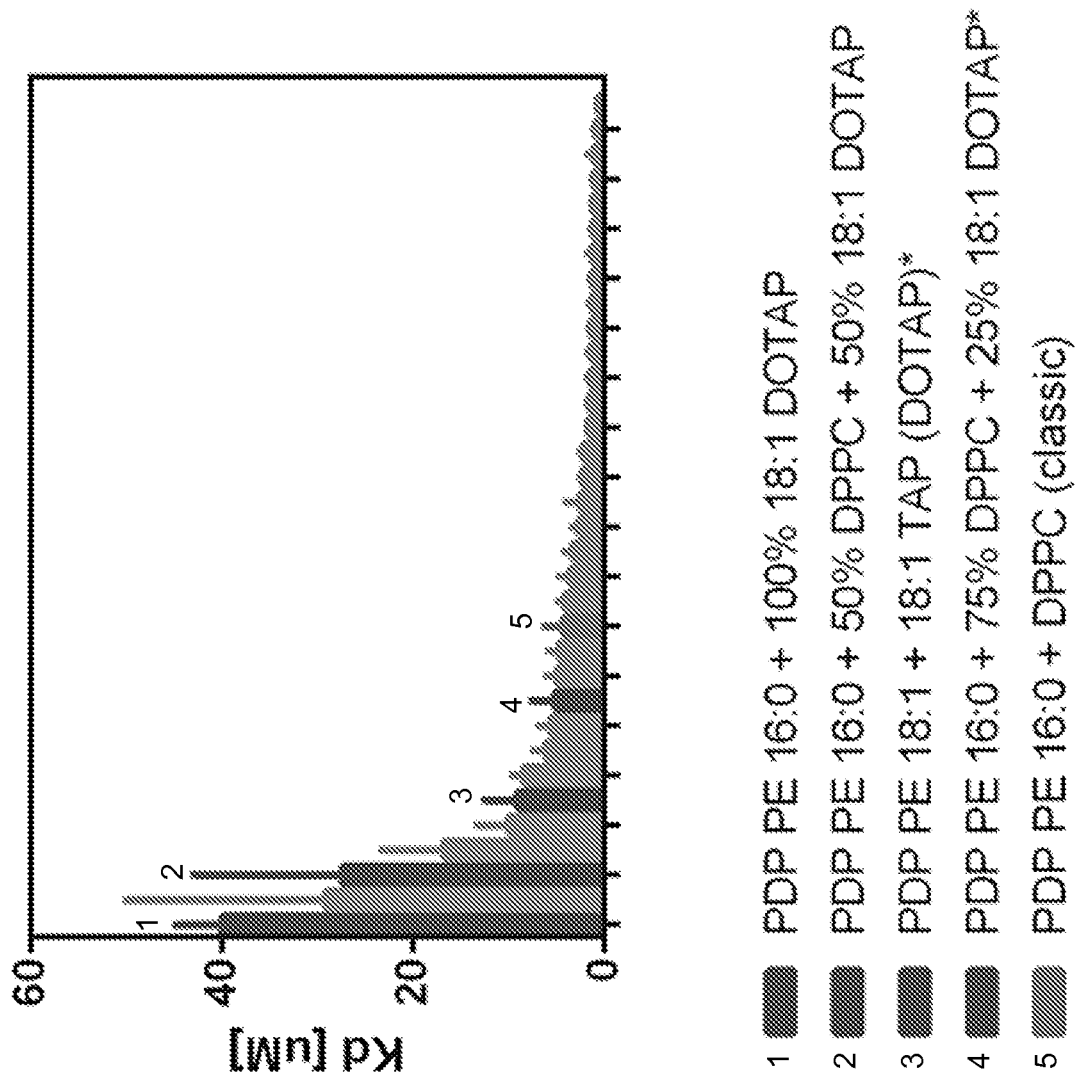
FIG. 17 depicts the dissociation constant, Kd [uM], between doxorubicin and different HDL NP constructs with indicated lipid composition (inner+outer lipid). PDP PE 16:0+100% 18:1 DOTAP; PDP PE 16:0+50% DPPC+18:1 DOTAP; PDP PE 18:1+18:1 TAP (DOTAP); PDP PE 16:0+ 75% DPPC+25% 18:1 DOTAP; AND PDP PE 16:0+DPPC (classic) were tested. Kd values were determined at room temperature in water. Constructs containing outer lipids with positively charged head groups are shown in color. High Kd values indicate low binding affinity.
Figure 18:
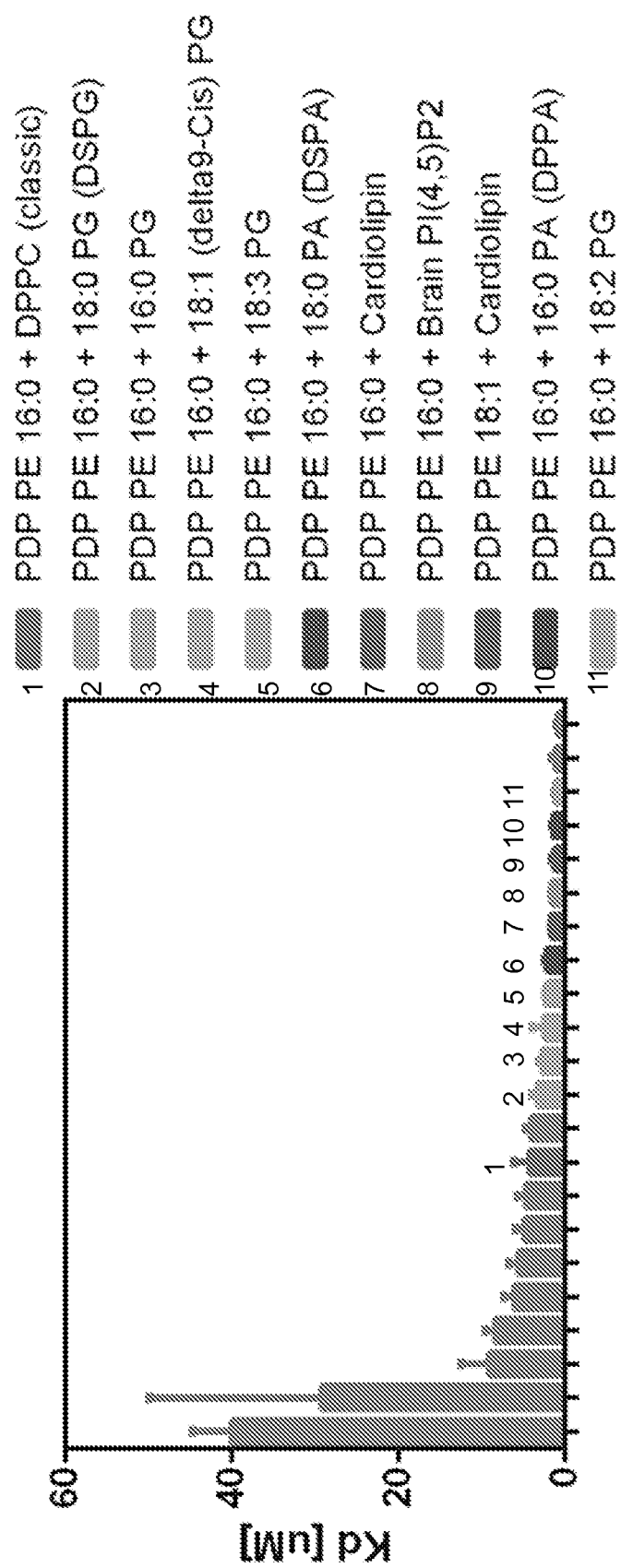
FIG. 18 shows the dissociation constant, Kd [uM]. between doxorubicin and different HDL NP constructs with indicated lipid composition (inner+outer lipid). PDP PE 16:0+DPPC (classic), PDP PE 16:0+18:0 (DSPG), PDP PE 16:0+16:0 PG, PDP PE 16:0+18:1 delta9-Cis PG, PDP PE 16:0+18:3 PG, PDP PE 16:0+18:0 PA (DSPA), PDP PE 16:0+cardiolipin, PDP PE 16:0+brain PI, PDP PE 16:0+16:0 PA, and PDP PE 16:0+18:2 PG were tested. Kd values were determined at room temperature in water. Constructs containing outer lipids with negatively charged head groups are shown in color. High Kd values indicate low binding affinity.

To further assess the flexibility of the HDL-NP platform for anticancer drug delivery, HDL-NP conjugates with vincristine, a widely used anticancer drug which interferes with microtubule formation, were synthesized. As with doxorubicin-HDL-NP, vincristine-HDL-NP was synthesized using 100-fold excess of vincristine in relation to the gold nanoparticle. Conjugates were incubated with Ramos and SUDHL-4 lymphoma cell lines for 48 hours and cell viability was assessed using the MTS assay. In both cell lines, vincristine-HDL-NP exhibit greater cytotoxicity when compared to either HDL-NP alone or free doxorubicin (FIG. 16), suggesting that the HDL-NP platform may be useful in formulating a variety of small molecule compounds for drug delivery.

REFERENCES

1. Yang, S.; Damiano, M. G.; Zhang, H.; Tripathy, S.; Luthi, A. J.; Rink, J. S.; Ugolkov, A. V.; Singh, A. T.; Dave, S. S.; Gordon, L. I.; Thaxton, C. S., Biomimetic, synthetic HDL nanostructures for lymphoma. *Proceedings of the National Academy of Sciences of the United States of America* 2013, 110 (7), 2511-6.
2. Cho, K.; Wang, X.; Nie, S.; Chen, Z. G.; Shin, D. M., Therapeutic nanoparticles for drug delivery in cancer. *Clinical cancer research: an official journal of the American Association for Cancer Research* 2008, 14 (5), 1310-6.
3. Rana, S.; Bajaj, A.; Mout, R.; Rotello, V. M., Monolayer coated gold nanoparticles for delivery applications. *Advanced drug delivery reviews* 2012, 64 (2), 200-16.
4. Akhter, S.; Ahmad, M. Z.; Ahmad, F. J.; Storm, G.; Kok, R. J., Gold nanoparticles in theranostic oncology: current state-of-the-art. *Expert opinion on drug delivery* 2012, 9 (10), 1225-43.
5. Shah, N. B.; Vercellotti, G. M.; White, J. G.; Fegan, A.; Wagner, C. R.; Bischof, J. C., Blood-nanoparticle interactions and in vivo biodistribution: impact of surface PEG and ligand properties. *Molecular pharmaceutics* 2012, 9 (8), 2146-55.
6. Bae, Y. H.; Park, K., Targeted drug delivery to tumors: myths, reality and possibility. *Journal of controlled release: official journal of the Controlled Release Society* 2011, 153 (3), 198-205.
7. McMahon, K. M.; Mutharasan, R. K.; Tripathy, S.; Veliceasa, D.; Bobeica, M.; Shumaker, D. K.; Luthi, A. J.; Helfand, B. T.; Ardehali, H.; Mirkin, C. A.; Volpert, O.; Thaxton, C. S., Biomimetic high density lipoprotein nanoparticles for nucleic acid delivery. *Nano letters* 2011, 11 (3), 1208-14.
8. Waterhouse, D. N.; Tardi, P. G.; Mayer, L. D.; Bally, M. B., A comparison of liposomal formulations of doxorubicin with drug administered in free form: changing toxicity profiles. *Drug safety: an international journal of medical toxicology and drug experience* 2001, 24 (12), 903-20.
9. Luthi, A. J.; Zhang, H.; Kim, D.; Giljohann, D. A.; Mirkin, C. A.; Thaxton, C. S., Tailoring of biomimetic high-density lipoprotein nanostructures changes cholesterol binding and efflux. *ACS nano* 2012, 6 (1), 276-85.
10. Daniel, M. C.; Astruc, D., Gold nanoparticles: assembly, supramolecular chemistry, quantum-size-related properties, and applications toward biology, catalysis, and nanotechnology. *Chemical reviews* 2004, 104 (1), 293-346.
11. (a) Dubertret, B.; Calame, M.; Libchaber, A. J., Single-mismatch detection using gold-quenched fluorescent oligonucleotides. *Nature biotechnology* 2001, 19 (4), 365-70; (b) Seferos, D. S.; Giljohann, D. A.; Hill, H. D.; Prigodich, A. E.; Mirkin, C. A., Nano-flares: probes for transfection and mRNA detection in living cells. *Journal of the American Chemical Society* 2007, 129 (50), 15477-9.

Example 5

Modified Components in Nanostructure

Through modification of the inner and outer lipid layer, the binding capacity as well as binding affinity of the HDL-NP for doxorubicin can be changed. For example, positively charged head groups in the outer layer decrease the binding affinity (17), while negatively charged lipid head groups increase the binding affinity (18).

Figure 19:
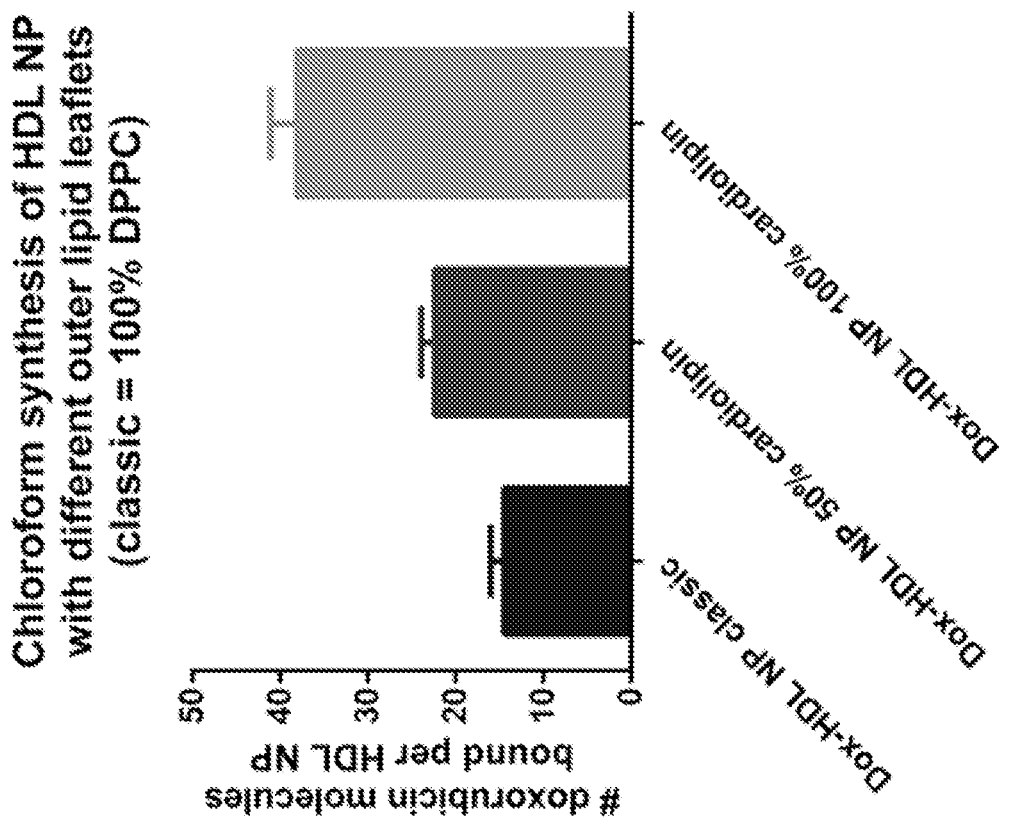
FIG. 19 depicts the number of doxorubicin molecules bound per HDL NP after purification, which was determined by denaturing the different Dox-HDL NPs through addition of acid and determining the amount of released doxorubicin utilizing the intrinsic fluorescence of doxorubicin.

Changes in the lipid composition of the HDL-NP can change the binding affinity between doxorubicin and the particle, as well as the binding capacity of the particle for doxorubicin (FIG. 19 and FIG. 20).

The binding affinity of HDL NP can further be altered by including cholesterol (the modulate fluidity of the lipid layer), poly(styrenesulfonate) (negatively charged polymer for enhanced doxorubicin binding), or DNA (with a doxorubicin binding motif) in the synthesis step.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

We claim:

1. A structure comprising:
a nanostructure core comprising an inorganic material;
a shell comprising a lipid layer surrounding and attached to the nanostructure core, the shell having an inner surface and an outer surface, wherein the shell has a therapeutic profile for a therapeutic agent, wherein the therapeutic agent is attached to the shell,
wherein the therapeutic profile is modified to regulate the binding capacity and/or the binding affinity between the therapeutic agent and the nanostructure;
a protein bound to at least the outer surface of the shell, wherein at least 80% of the lipids in the outer surface of the shell have negatively charged head groups, and wherein 20-400 therapeutic agents are associated per structure; and
wherein the inner surface of the shell comprises PDP PE 16:0 or PDP PE 18:1.

2. The structure of claim 1 wherein the lipid layer is a lipid bilayer.

3. The structure of claim 2 wherein the protein is an apolipoprotein.

4. The structure of claim 2 wherein the therapeutic profile is associated with the outer surface of the shell.

5. The structure of claim 1, wherein the therapeutic profile is lipids in the outer surface of the shell having negative head groups.

6. The structure of claim 5, wherein at least 95% of the lipids in the outer surface of the shell have negatively charged head groups.

7. The structure of claim 5, wherein the lipids in the outer surface of the shell are selected from the group consisting of 18:0 PG (1,2-Distearoyl-sn-glycero-3-phosphoglycerol), 16:0 PG (1,2-dipalmitoyl-sn-glycero-3-phospho-(1'-rac-glycerol)), 18:1 delta9-Cis PG, 18:3 PG (1,2-dilinolenoyl-sn-glycero-3-phospho-(1'-rac-glycerol)), 18:0 PA (1,2-Distearoyl-sn-glycero-3-phosphate), cardiolipin, brain PI (phosphatidylinositol), 16:0 PA (1,2-Dipalmitoyl-sn-glycero-3-phosphate), and 18:2 PG (1,2-dilinoleoyl-sn-glycero-3-phospho-(1'-rac-glycerol)).

8. The structure of claim 1, wherein the therapeutic profile is lipids in the outer surface of the shell having mixtures of negative and neutral head groups.

9. The structure of claim 1, wherein the therapeutic profile is lipids in the outer surface of the shell having mixtures of positive and neutral head groups.

10. The structure of claim 1, wherein the therapeutic profile is lipids in the outer surface of the shell having mixtures of negative and positive head groups.

11. The structure of claim 1, wherein the therapeutic profile is lipids in the outer surface of the shell having mixtures of negative, positive and neutral head groups.

12. The structure of claim 1, wherein the shell comprises lipids and the lipids in the shell are selected from the group consisting of phospholipids, unsaturated lipids, saturated lipids, and therapeutic lipids.

13. The structure of claim 1, wherein the therapeutic agent is selected from the group consisting of an anti-infectious disease agent, a chemotherapeutic agent, another type of anti-cancer agent, an anti-immunological disease agent, an anti-vascular disease agent, and an anti-rheumatologic disease agent.

14. A structure comprising:
a nanostructure core comprising an inorganic material;
a shell comprising a lipid layer surrounding and attached to the nanostructure core, the shell having an inner surface and an outer surface;
an apolipoprotein bound to at least the outer surface of the shell; and
a therapeutic agent adsorbed on the outer shell and/or incorporated between the inner surface and outer surface of the shell, wherein the therapeutic agent is selected from the group consisting of andrographolide and vincristine,
wherein at least 80% of the lipids in the outer surface of the shell have negatively charged head groups.

15. A method of treating a disease with reduced toxicity, comprising
administering to a subject having a disease a nanostructure comprising a core, a shell comprising a lipid layer surrounding and attached to the core, the shell having an inner surface and an outer surface; an apolipoprotein associated with the shell and a therapeutic agent having toxic properties in order to treat the disease, while causing less toxicity than the toxicity caused by treatment of a subject having the disease with the therapeutic agent alone,
wherein the disease is a cancer that expresses scavenger receptor type B-,
wherein toxicity is cardiotoxicity,
wherein 20-400 therapeutic agents are associated per structure, and
wherein the inner surface of the shell comprises PDP PE 16:0 or PDP PE 18:1.

16. The structure of claim 13, wherein the chemotherapeutic agent is doxorubicin, andrographolide, or vincristine.

17. The structure of claim 1, wherein the inner surface of the shell comprises PDP PE 16:0 and the outer surface of the shell comprises a lipid selected from a group consisting of 18:0 PG (1,2-Distearoyl-sn-glycero-3-phosphoglycerol), 16:0 PG (1,2-dipalmitoyl-sn-glycero-3-phospho-(1'-rac-glycerol)), 18:1 delta9-Cis PG, 18:3 PG (1,2-dilinolenoyl-sn-glycero-3-phospho-(1'-rac-glycerol)), 18:0 PA (1,2-Distearoyl-sn-glycero-3-phosphate), cardiolipin, brain PI (phosphatidylinositol), 16:0 PA (1,2-Dipalmitoyl-sn-glycero-3-phosphate), and 18:2 PG (1,2-dilinoleoyl-sn-glycero-3-phospho-(1'-rac-glycerol)).

18. The structure of claim 1, wherein the inner surface of the shell comprises PDP PE 18:1 and cardiolipin.

19. The structure of claim 1, wherein the inner surface of the shell comprises PDP PE 18:1 and wherein the shell comprises:
  (i) sphingomyelin; or
  (ii) cardiolipin, 16:0 PA (1,2-Dipalmitoyl-sn-glycero-3-phosphate), and 18:2 PG (1,2-dilinoleoyl-sn-glycero-3-phospho-(1'-rac-glycerol)).

* * * * *

UNITED STATES PATENT AND TRADEMARK OFFICE
CERTIFICATE OF CORRECTION

PATENT NO. : 10,568,898 B2
APPLICATION NO. : 14/911957
DATED : February 25, 2020
INVENTOR(S) : C. Shad Thaxton et al.

It is certified that error appears in the above-identified patent and that said Letters Patent is hereby corrected as shown below:

In the Specification

At Column 1, Line 11 please add the following paragraph after the paragraph RELATED APPLICATIONS:
FEDERALLY SPONSORED RESEARCH
This invention was made with government support under grant number EEC0647560 awarded by the National Science Foundation. The government has certain rights in the invention.

Signed and Sealed this
Twenty-fourth Day of September, 2024

Katherine Kelly Vidal
*Director of the United States Patent and Trademark Office*